(12) United States Patent
Horie et al.

(10) Patent No.: US 6,791,334 B2
(45) Date of Patent: Sep. 14, 2004

(54) OIL CONDITION SENSOR AND METHOD FOR MAKING THE SAME

(75) Inventors: Kazuyuki Horie, Nagoya (JP); Kiwamu Naito, Chita-gun (JP)

(73) Assignee: Denso Corporation (JP)

( * ) Notice: Subject to any disclaimer, the term of this patent is extended or adjusted under 35 U.S.C. 154(b) by 85 days.

(21) Appl. No.: 10/078,425

(22) Filed: Feb. 21, 2002

(65) Prior Publication Data

US 2002/0113596 A1 Aug. 22, 2002

(30) Foreign Application Priority Data

| Feb. 22, 2001 | (JP) | ................................. | 2001-046530 |
| Mar. 19, 2001 | (JP) | ................................. | 2001-078062 |
| Mar. 19, 2001 | (JP) | ................................. | 2001-078066 |
| Jul. 3, 2001 | (JP) | ................................. | 2001-202710 |
| Nov. 30, 2001 | (JP) | ................................. | 2001-366021 |
| Dec. 17, 2001 | (JP) | ................................. | 2001-383366 |

(51) Int. Cl.[7] ..................... G01N 27/416; G01N 33/26
(52) U.S. Cl. ................... 324/438; 324/717; 73/53.05
(58) Field of Search ............... 324/438, 698, 324/715, 717; 73/53.05; 29/592.1, 825

(56) References Cited

U.S. PATENT DOCUMENTS

| 4,635,473 | A | * | 1/1987 | Hochstein ................. 73/118.1 |
| 5,089,780 | A | * | 2/1992 | Megerle ..................... 324/698 |
| 5,146,169 | A | * | 9/1992 | Morishita et al. ........... 324/438 |
| 5,523,692 | A |   | 6/1996 | Kuroyanagi et al. ........ 324/438 |
| 5,635,845 | A | * | 6/1997 | Strong et al. ............... 324/717 |
| 5,789,665 | A | * | 8/1998 | Voelker et al. ............ 324/698 |
| 5,929,754 | A | * | 7/1999 | Park et al. ................. 73/53.05 |
| 6,549,015 | B2 | * | 4/2003 | Horie et al. ................ 324/438 |

FOREIGN PATENT DOCUMENTS

| JP | 5-5720 | 1/1993 |
| JP | 6-281619 | 10/1994 |
| JP | 7-77514 | 3/1995 |
| JP | 7-140111 | 6/1995 |

* cited by examiner

*Primary Examiner*—N. Le
*Assistant Examiner*—Timothy J. Dole
(74) *Attorney, Agent, or Firm*—Nixon & Vanderhye PC

(57) ABSTRACT

An oil condition sensor detects a condition of oil in response to the potential difference between electrodes. The electrodes include at least a first and second electrodes coaxially arranged. The electrodes have projections being arranged to face each other in an opposed manner. Therefore, the projections provide wide surface area that performs as electrodes. It is possible to provide compact oil condition sensor that is easy to install into an oil tank or oil pan.

36 Claims, 31 Drawing Sheets

OIL CONDITION SENSOR AND METHOD FOR MAKING THE SAME

CROSS REFERENCE TO RELATED APPLICATION

This application is based on Japanese Patent Applications No. 2001-46530 filed on Feb. 22, 2001, No. 2001-78062 filed on Mar. 19, 2001, No. 2001-78066 filed on Mar. 19, 2001, No. 2001-202710 filed on Jul. 3, 2001, No. 2001-366021 filed on Nov. 30, 2001 and No. 2001-383366 filed on Dec. 17, 2001 the contents of which are incorporated herein by reference.

BACKGROUND OF THE INVENTION

1. Field of the Invention

The present invention relates to an oil condition sensor which detects the condition of oil.

2. Description of the Related Art

Along with the use of oil for hydraulic control or lubrication served for vehicle or the like, a foreign material is mixed into oil or oil is degraded as time lapses. The PH value which indicates acidity or alkalinity of oil can indicate a condition of oil. The change of PH value expresses the deterioration of the condition of oil. Accordingly, the oil exchange period can be known by detecting the condition of oil. For example, an oil condition sensor which detects the condition of oil can be constituted of a reference electrode whose potential is held at a substantially fixed value irrespective of the PH value of oil and a comparison electrode whose potential is changed in response to the PH value of oil. When the PH value of oil is changed along with the deterioration of oil, the potential difference between both electrodes is changed.

JP-A-7-77514 discloses a conventional oil condition sensor. But the sensor has a drawback that the number of parts is increased so that the man-hours for assembling is increased. JP-A-6-281619, JP-A-7-140111, JP-A-5-5720 and U.S. Pat. No. 5,523,692 also disclose oil condition sensors. However, it has been difficult to obtain the compact configuration and the wide electrode area. Further, these publications fail to disclose practical structures.

In general, when the current leaks between electrodes, the accuracy of measuring potential between the electrodes is lowered and hence, the reliable insulation between the electrodes is required. Further, when the resistance between the electrodes of the oil condition sensor is large, the accuracy of measuring potential between the electrodes is lowered and hence, it is necessary to lower the resistance between the electrodes.

SUMMARY OF THE INVENTION

It is an object of the present invention to provide an oil condition sensor which can reduce the number of parts, can miniaturize the sensor and can detect the condition of oil and a method for making the oil condition sensor.

It is another object of the present invention to provide a miniaturized oil condition sensor which can detect an oil level in addition to the condition of oil.

According to the oil condition sensor of the present invention, respective electrodes are formed in a cylindrical shape. Therefore, the number of parts can be decreased and the man-hours for assembling can be reduced. Further, the detection accuracy of the condition of oil can be enhanced without increasing the size or diameter of the oil condition sensor.

Each electrode may be provided with communication holes which allow the inside and the outside thereof to communicate with each other. Since oil flows between the inside and the outside through the communication holes, it is possible to improve an oil circulation between the electrodes whereby the condition of oil can be detected with high accuracy.

The oil level sensor may be provided to the inside of the electrode. Due to such a constitution, man-hours for mounting the sensors on an oil pan or the like can be decreased. Further, insertion holes which are served for allowing the insertion of the sensors provided with a condition sensor and the oil level sensor into the oil pan from the outside can be made small.

With respect to mounting portions of both electrodes, at least one of the mounting portions may be bent to be away from the other mounting portion. Since the surface distance of a support member from one mounting portion to the other mounting portion, that is, the creepage distance can be elongated, a leak current can be reduced.

BRIEF DESCRIPTION OF THE DRAWINGS

Features and advantages of embodiments will be appreciated, as well as methods of operation and the function of the related parts, from a study of the following detailed description, the appended claims, and the drawings, all of which form a part of this application. In the drawings:

DETAILED DESCRIPTION OF PREFERRED EMBODIMENTS

A plurality of embodiments of the present invention will be explained hereinafter with reference to the drawings.
(First Embodiment)

An oil condition sensor 10 is mounted on an oil pan of a vehicle, for example, and detects the condition of oil used for hydraulic control and lubrication.

Figure 3A:
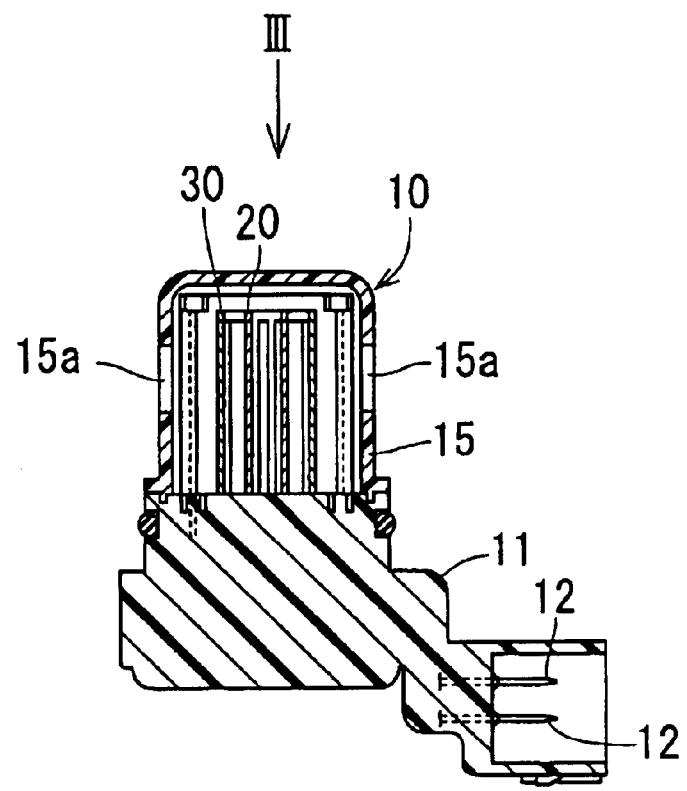
FIG. 3A is a cross-sectional view showing the oil condition sensor of the first embodiment.
Figure 3B:
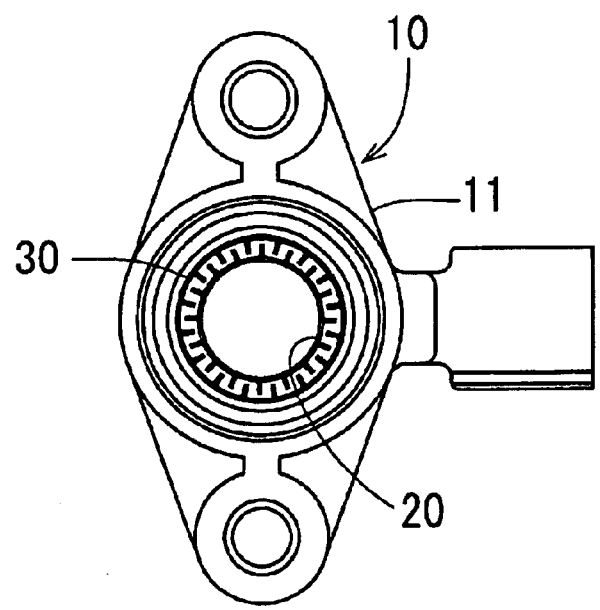
FIG. 3B is a view as viewed from an arrow direction III in FIG. 3A in the state that a cover is removed.

A first electrode 20 and a second electrode 30 are formed in a cylindrical shape and are mounted on a support member 11 made of insulation resin or the like using an adhesive agent or the like as shown in FIG. 3. The first electrode 20 and the second electrode 30 are immersed in oil filled in an oil pan or the like. The second electrode 30 is arranged outside the first electrode 20 coaxially with the first electrode 20. One of these electrodes is formed of metal whose potential is substantially fixed irrespective of the PH value of oil and the other electrode is formed of metal whose potential is changed in response to the PH value of oil.

Terminals 12 which are electrically connected with respective electrodes are embedded into the support member 11. A cover 15 is coupled or connected to the support member 11 so as to cover the first electrode 20 and the second electrode 30. Communication holes 15a are formed in the cover 15 to allow the communication of oil between the inside and the outside of the cover 15.

The first electrode 20 is formed in a cylindrical shape and includes fins 21 which constitute first projections projecting radially outwardly toward the second electrode 30 and extending in the axial direction. Between the neighboring fins 21 and 21 which are arranged in the circumferential direction, communication holes 25 which allow the inside and the outside of the first electrode 20 to communicate with each other and enable the flow of oil between inside and the outside of the first electrode 20 are formed.

The second electrode 30 is formed in a cylindrical shape and includes fins 31 which constitute second projections projecting radially inwardly toward the first electrode 20 and extending in the axial direction. The projecting direction of the fins 31 is displaced or offset from the projecting direction of the fins 21. Between the neighboring fins 31 and 31 which are arranged in the circumferential direction, communication holes 35 which allow the inside and the outside of the second electrode 30 to communicate with each other and enable the flow of oil between the inside and the outside of the second electrode 30 is formed.

Since the oil flows between the insides and the outsides of the respective electrodes through the communication holes 25 and the communication holes 35, the oil is prevented from dwelling in the peripheries of both electrodes. Accordingly, the deterioration condition of the whole oil can be detected with high accuracy.

Figure 1:
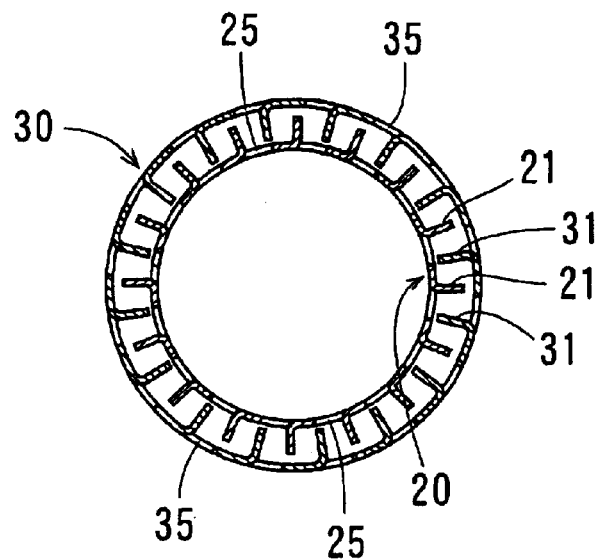
FIG. 1 is a cross-sectional view showing electrodes of an oil condition sensor according to the first embodiment of the present invention.
Figure 2:
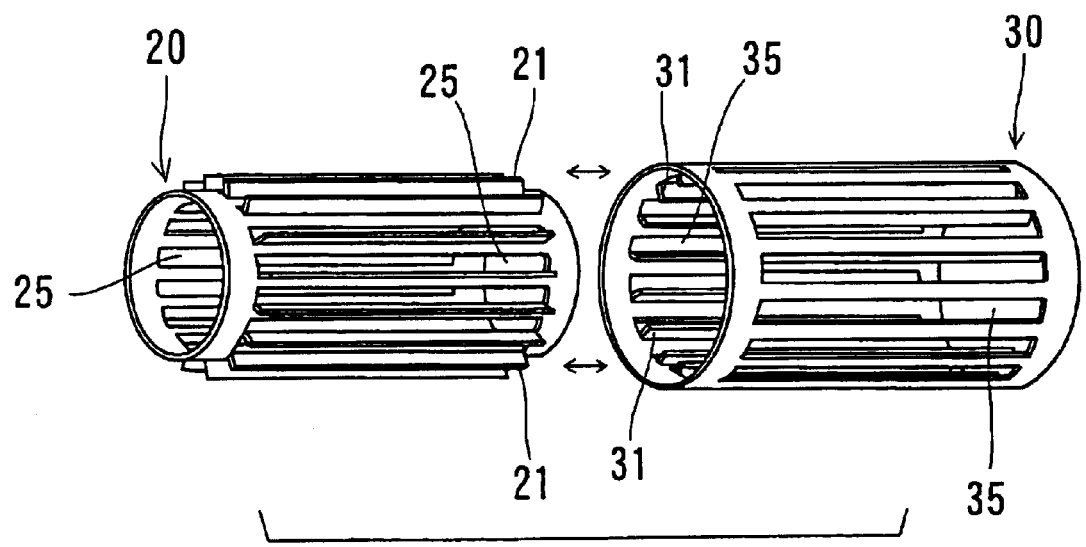
FIG. 2 is an exploded perspective view showing the electrodes of the first embodiment.

In the state that the first electrode 20 and the second 30 are assembled as shown in FIG. 1, the fins 31 are positioned at both sides of the fin 21 in the circumferential direction, while the fins 21 are positioned at both sides of the fin 31 in the circumferential direction. That is, the fin 21 faces two fins 31 in an opposed manner and the fin 31 faces two fins 21 in an opposed manner. Further, an outer peripheral surface of the first electrode 20 faces an inner peripheral surface of the second electrode 30 in an opposed manner in a radial direction. Accordingly, the facing areas of the first electrode 20 and the second electrode 30 are increased. When the facing areas of both electrodes are increased, the resistance between the electrodes is decreased so that the condition of oil can be detected with high accuracy.

Figure 4A:
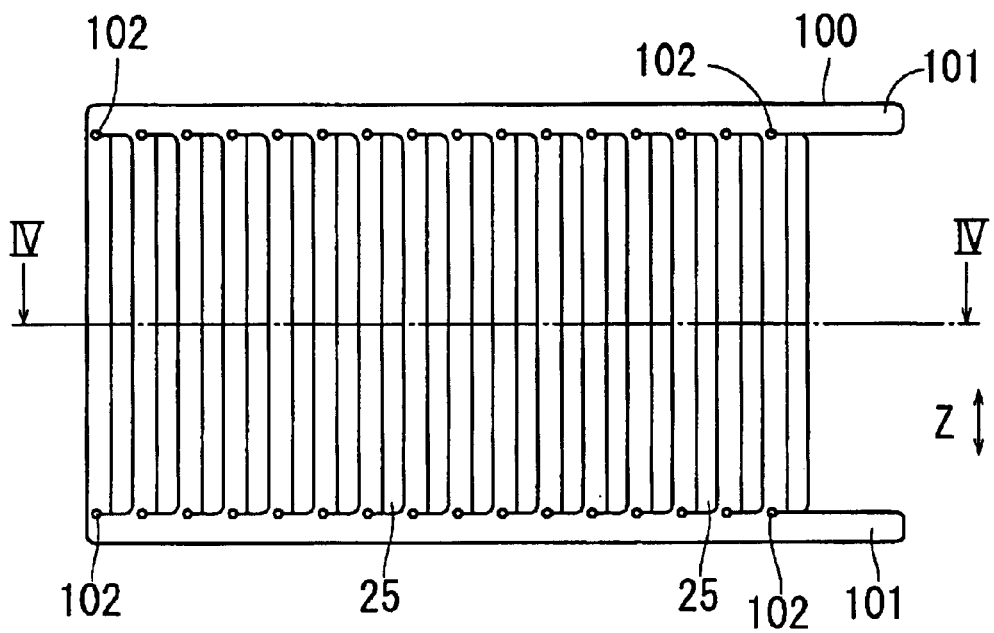
FIG. 4A is a plan view showing a first electrode pre-form of the first embodiment.
Figure 4B:
FIG. 4B is a cross-sectional view taken along a line IV—IV of FIG. 4A.
Figure 6A:
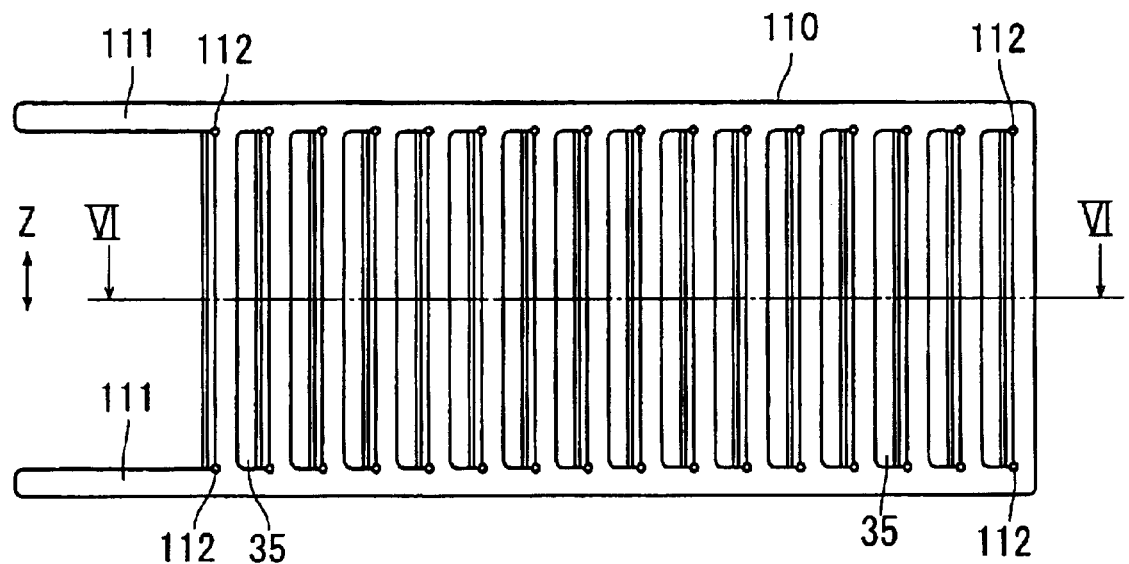
FIG. 6A is a plan view showing a second electrode pre-form of the first embodiment.
Figure 6B:
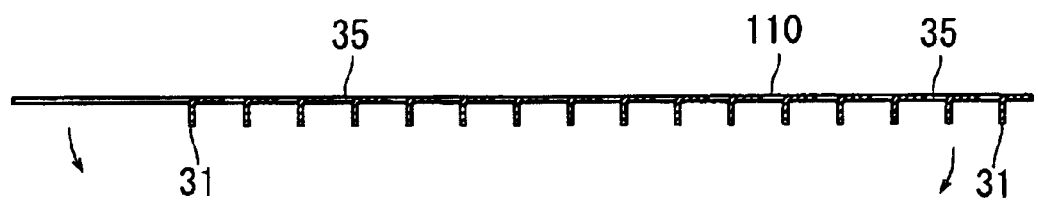
FIG. 6B is a cross-sectional view taken along a line VI—VI of FIG. 6A.

Subsequently, the manufacturing method of the first electrode 20 and the second electrode 30 is explained. As shown in FIG. 4A and FIG. 6A, a first electrode pre-form 100 and a second electrode pre-form 110 are made of rectangular thin plates. The first electrode pre-form 100 and the second electrode pre-form 110 include strips 101 and 111 which are welded when the first electrode pre-form 100 and the second electrode pre-form 110 are rounded to form a cylindrical shape and to maintain such a cylindrical shape.

In the first step, before forming the fins 21 and 31 and the communication holes 25 and 35, through holes 102 and 112 are formed in both Z-directional end sides of both pre-forms which are positioned at portions where the fins 21 and 31 are formed.

In the second step, a set of comb-shaped punching or blanking molds not shown in the drawing which have blades extending in the Z direction which is the width direction of both pre-forms are engaged with each other from one-surface side and the other-surface side of both pre-forms in which the through holes 102 and 112 are formed so that the fins 21 and 31 and the communication holes 25 and 35 are formed in the first electrode pre-form 100 and the second electrode pre-form 110.

Figure 5:
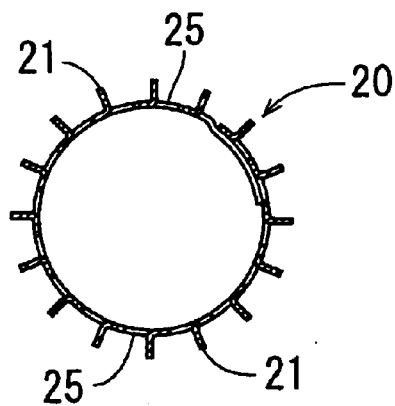
FIG. 5 is a cross-sectional view showing the first electrode.
Figure 7:
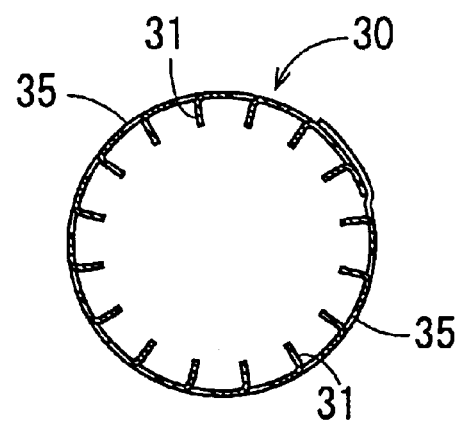
FIG. 7 is a cross-sectional view showing the second electrode.

In the third step, the first electrode pre-form 100 which is formed as shown in FIG. 4A is rounded to form a cylindrical shape such that the fins 21 are directed outwardly and the longitudinally extending direction of the fins 21 is aligned with the axial direction of the cylinder. Thereafter, the strips 101 and portions of the pre-form 100 other than the strip 101 are welded together to form the first electrode 20 shown in FIG. 5. Further, the second electrode pre-form 110 which is formed as shown in FIG. 6A is rounded to form a cylindrical shape such that the fins 31 are directed inwardly and the extending direction of the fins 31 is aligned with the axial direction of the cylinder and, thereafter, the strips 111 and portions of the pre-form 110 other than the strip 111 are welded together to form the second electrode 30 shown in FIG. 7.

In the fourth step, the first electrode 20 and the second electrode 30 are assembled such that. the fins 21 and the fins 31 are alternately positioned in the circumferential direction.

Besides the above-mentioned manufacturing method, it may possible to adopt a manufacturing method in which an inner cylinder having a pipe shape and an outer cylinder having a pipe shape and a diameter larger than a diameter of the inner cylinder are prepared, fins directed outwardly are formed on the inner cylinder and fins directed inwardly are formed on the outer cylinder, and thereafter, the inner and outer cylinders are assembled to each other.

(Second Embodiment)

Figure 8:
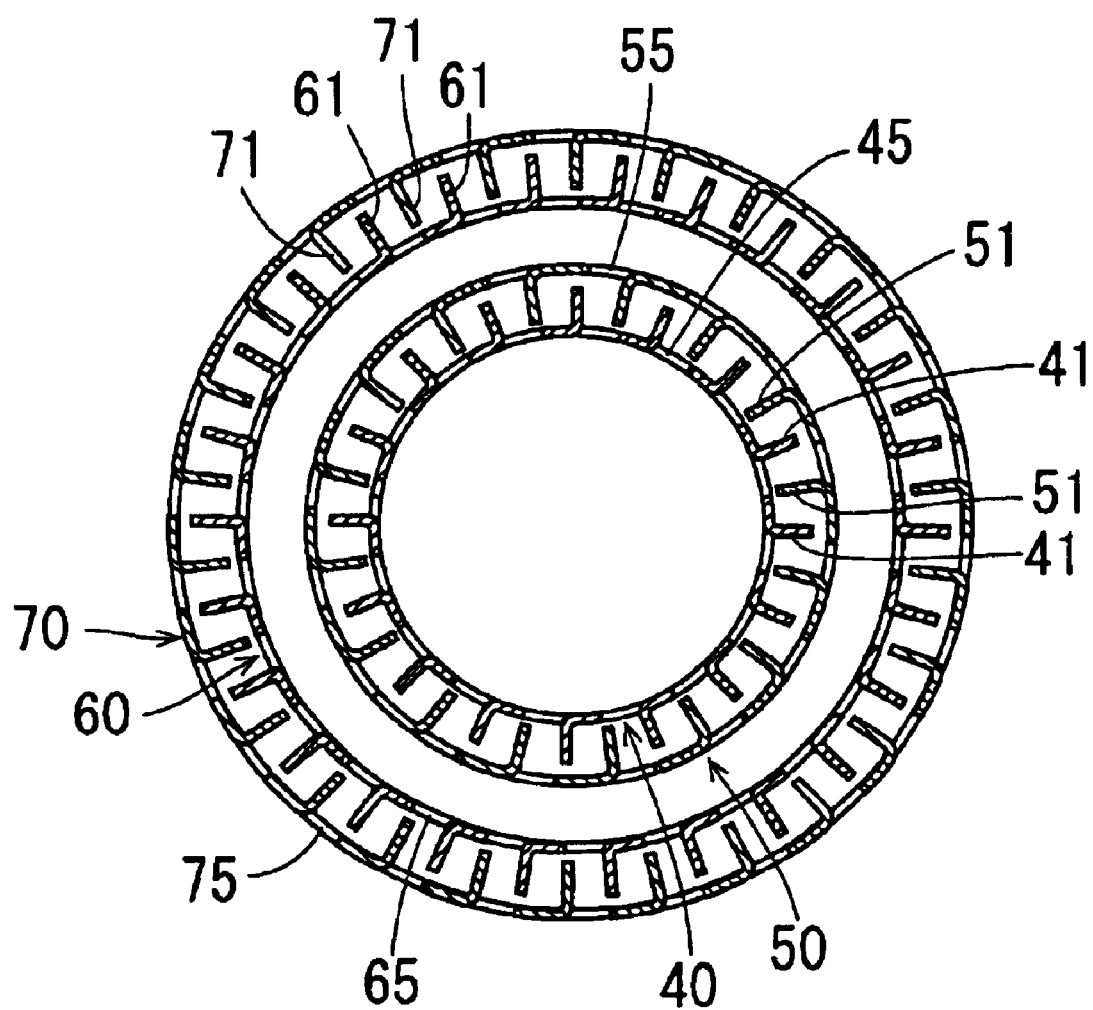
FIG. 8 is a cross-sectional view showing electrodes of an oil condition sensor according to the second embodiment of the present invention.

The second embodiment of the present invention is shown in FIG. 8. In the embodiments which will be explained hereinafter, parts which are substantially identical with those of the first embodiment are indicated by same numerals. The manufacturing methods of respective electrodes are as same as the manufacturing method of the first embodiment.

First electrodes 40 and 60 and second electrodes 50 and 70 are respectively formed in a cylindrical shape, wherein the first electrode 40 and the second electrode 50 are arranged coaxially and the first electrode 60 and the second electrode 70 are arranged coaxially. Further, the first electrode 40 and the second electrode 50 constitute a pair of electrodes. The first electrode 60 and the second electrode 70 constitute another pair of electrodes. Two pairs of electrodes are arranged coaxially.

The diameters of respective electrodes are increased in the ascending order of the first electrode 40, the second electrode 50, the first electrode 60 and the second electrode 70, wherein the second electrodes 50 and 70 are respectively arranged outside the first electrodes 40 and 60. The first electrodes 40 and 60 respectively have fins 41 and 61 which constitute first projections extending radially outwardly toward the second electrodes 50 and 70. The second electrodes 50 and 70 respectively have fins 51 and 71 which constitute second projections extending radially inwardly toward the first electrodes 40 and 60. Between the neighboring fins of respective electrodes in the circumferential direction, communication holes 45, 55, 65 and 75 which make the inside and the outside of respective electrodes communicate with each other and allow oil to flow between the inside and the outside of respective electrodes are formed.

In the state shown in FIG. 8 in which respective electrodes are assembled to each other, the fins 51 and 71 are respectively positioned at both sides of the fins 41 and 61 in the circumferential direction, while the fins 41 and 61 are respectively positioned at both sides of the fins 51 and 71 in the circumferential direction. That is, the fins 41 and 61 respectively face two fins 51 and 71 in an opposed manner, while the fins 51 and 71 respectively face two fins 41 and 61 in an opposed manner.

Further, the outer peripheral surfaces of the first electrodes 40 and 60 respectively face the inner peripheral surfaces of the second electrodes 50 and 70 in an opposed manner in the radial direction. Still further, the outer peripheral surface of the second electrode 50 faces the inner peripheral surface of the first electrode 60 in an opposed manner in the radial direction. Accordingly, the facing areas of the first electrodes 40 and 60 and the second electrodes 50 and 70 are increased. When the facing areas of the first electrodes 40 and 60 and the second electrodes 50 and 70 are increased, the resistance between the electrodes is reduced so that the condition of oil can be detected with high accuracy.

(Third Embodiment)

Figure 9:
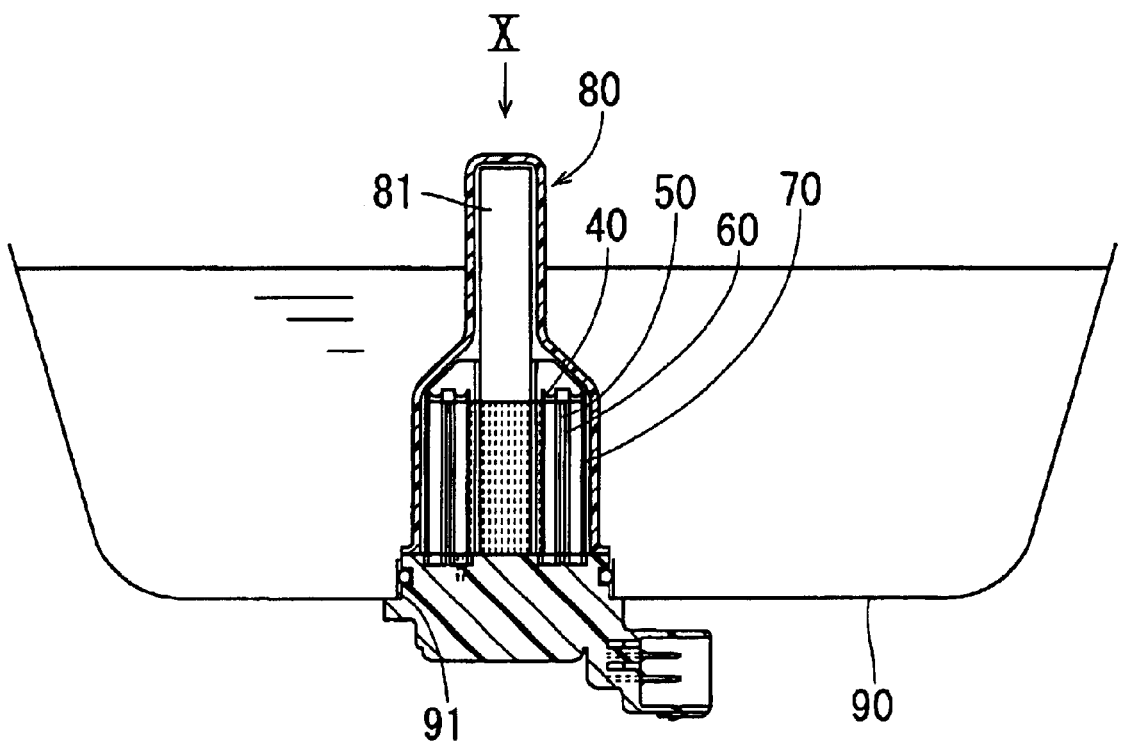
FIG. 9 is a cross-sectional view showing a state in which an oil condition sensor according to the third embodiment of the present invention is mounted on an oil pan.
Figure 10:
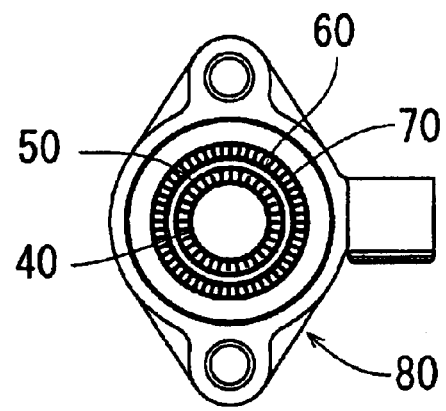
FIG. 10 is a view of an oil condition sensor in the state that a cover is removed in FIG. 9 as viewed from a direction of an arrow X.

The third embodiment of the present invention is shown in FIG. 9 and FIG. 10. Parts which are substantially identical with those of the above-mentioned embodiments are indicated by same numerals.

An oil condition sensor 80 of the third embodiment includes the first electrodes 40 and 60 and the second electrodes 50 and 70 shown in the second embodiment and an oil level sensor 81 which detects an oil level. The oil level sensor 81 is a known oil level sensor which detects an oil level, wherein the oil level sensor 81 is disposed at the inside of the first electrode 40 which constitutes the innermost electrode. The oil condition sensor 80 is inserted into the oil pan 90 through an insertion hole 91 of the oil pan 90 from the outside of the oil pan 90 such that respective electrodes and the oil level sensor 81 are immersed in the oil filled in the oil pan 90.

Since the respective electrodes which constitute the condition sensor and the oil level sensor which detects an oil level are incorporated into the single oil condition sensor 80, the man-hours for mounting of both sensors can be decreased compared to a case in which the condition sensor and the oil level sensor are separately mounted on the oil pan 90.

Further, since the oil level sensor 81 is disposed in the inside of the first electrode 40 which constitutes the innermost electrode, it is possible to prevent the diameter of the oil condition sensor 80 from being increased. Accordingly, the diameter of the insertion hole 91 served for allowing the insertion of the oil condition sensor 80 into the oil pan 90 can be decreased.

(Fourth Embodiment)

Figure 11:
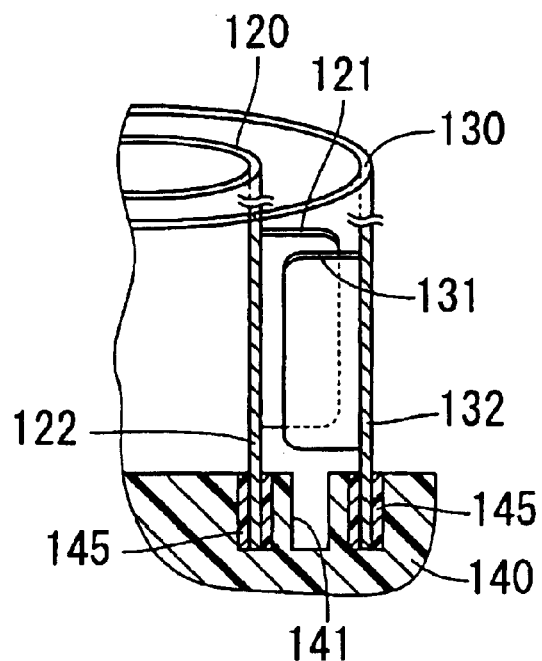
FIG. 11 is a schematic cross-sectional view showing an oil condition sensor according to the fourth embodiment of the present invention.

The fourth embodiment of the present invention is shown in FIG. 11. A first electrode 120 of the fourth embodiment shares the same constitution with the first electrode 20 of the first embodiment and a second electrode 130 of the fourth embodiment shares the same constitution with the second electrode 30 of the first embodiment. In the fourth embodiment, fins 121 which constitute first projections and fins 131 which constitute second projections have mounting portions 122 and 132 thereof. The mounting portions 122 and 132 constitute cylindrical end portions fixedly secured to a support member 140 made of insulation resin by means of an adhesive agent 145. The fins 121 and 131 are disposed away from the support member 140 and hence, the fins 121 and 131 are not brought into contact with the support member 140.

On a surface of the support member 140 of a side on which the mounting portions 122 and 132 of both electrodes are mounted, an uneven surface is formed between the mounting portion 122 and the mounting portion 132. In this embodiment, an annular recess (groove) 141 provides the uneven surface. The recess 141 provides longer surface distance between the electrodes 120 and 130. The longer surface distance reduces leakage current. The recess 141 provides at least one of vertical surface between the electrodes 120 and 130. The vertical surface avoids depositing of conductive sediment. Therefore, the vertical surface is kept clean and provides reliable insulation, even if conductive sediment is deposited between the electrodes.

Since the fins 121 and 131 are not brought into contact with the support member 140, it is possible to prevent the leaking of current between the fin 121 and the fin 131 through the support member 140. Further, since the recessed portion 141 is formed between the mounting portion 122 and the mounting portion 132, the surface distance of the support member 140 between the mounting portion 122 and the mounting portion 132, that is, the creepage distance can be elongated. Even when a conductive foreign material which is mixed in oil, for example, is adhered to the surface of the support member 140 which is positioned between both mounting portions 122 and 132, the creepage distance of the support member 140 is elongated and hence, it is possible to prevent the flow of electricity between the mounting portion 122 and the mounting portion 132 through the foreign material. Since it is possible to prevent the flow of leak current between the mounting portion 122 and the mounting portion 132, that is, between the electrode 120 and the electrode 130, the accuracy of detection of potential between the electrodes can be enhanced.

The recess 141 may is replaceable with an annular protrusion, a V-shaped groove or a step. An inclined surface provided by the V-shaped groove is also effective to avoid depositing sediment. A single step is also effective to provide an inclined or vertical surface.

In the first, second, third and fourth embodiments, the fins are formed on the first electrode and the second electrode which are respectively formed into a cylindrical shape, and in addition to the oppositely-facing relationship between the outer peripheral surface of the first electrode and the inner peripheral surface of the second electrode, the fins of the first electrode and the fins of the second electrode which are arranged alternately in the circumferential direction face each other in an opposed manner. Accordingly, the facing areas of the electrodes can be increased so that the resistance between the electrodes is decreased whereby the condition of oil can be detected with high accuracy.

Further, since the respective electrodes are formed by pressing a single thin sheet, the number of parts of the oil condition sensor can be reduced whereby the number of man-hours for manufacturing the oil condition sensor can be reduced.

Although the fins are extended in the axial direction of respective electrodes which are formed in a cylindrical shape in the above-mentioned plural embodiments, fins which are extended in a spiral manner may be formed. Further, although respective electrodes may be formed by forming corrugated sheets in a cylindrical shape. Further, although respective electrodes are formed in a cylindrical shape, any polygonal shape can be adopted as the shape of the respective electrodes provided that the shape is a cylindrical shape. Further, although respective electrodes are formed by blanking the thin sheet by a press and rounding the blanked thin sheet, the respective electrodes may be formed by cutting metal in a cylindrical shape and forming projections. Still further, electrodes may be formed by extruding an inner cylinder and an outer cylinder having fins in the axial direction.

(Fifth Embodiment)

Figure 12:
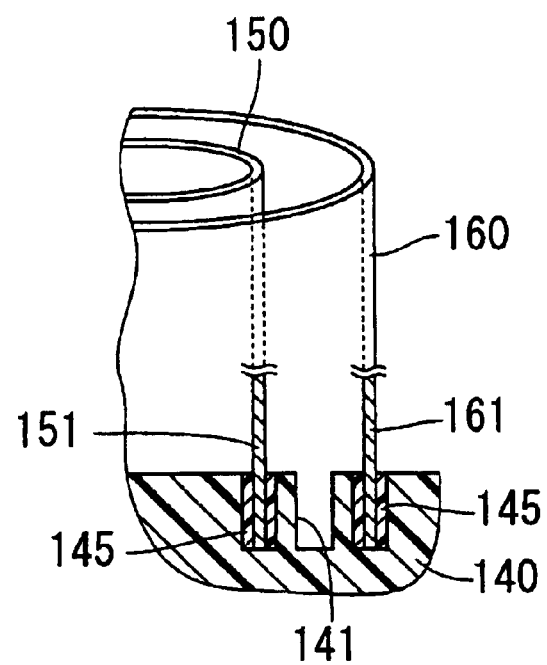
FIG. 12 is a schematic cross-sectional view showing an oil condition sensor according to the fifth embodiment of the present invention.

A first electrode 150 and a second electrode 160 of the fifth embodiment shown in FIG. 12 may be provided with fins having a shape equal to or different from a shape of the fins of the first electrode 120 and the second electrode 130 of the fourth embodiment. Further, although both electrodes are depicted in a cylindrical shape, both electrodes may be formed in a planer shape, an L-letter shape or the like. Still further, both electrodes may be constituted of lamination-type electrodes. On a surface of the support member 140 at a side on which mounting portions 151 and 161 are formed, in the same manner as the fourth embodiment, a recessed portion 141 is formed between the mounting portion 151 and the mounting portion 161.

The first electrode 150 and the second electrode 160 have the mounting portion 151 and the mounting portion 161 thereof fixedly secured to the support member 140 by means of an adhesive agent 145, wherein portions other than the mounting portions 151 and 161 are disposed away from the support member 140 and hence, these portions are not brought into contact with the support member 140. Further, in the same manner as the fourth embodiment, since the recessed portion 141 is formed in the surface of the support member 140 which is positioned between the mounting portion 151 and the mounting portion 161, a creepage distance of the support member 140 is elongated. Accordingly, it is possible to prevent a leak current from flowing between the first electrode 150 and the second electrode 160 so that the accuracy of detection of the potential between the electrodes can be enhanced.

(Sixth Embodiment)

Figure 13:
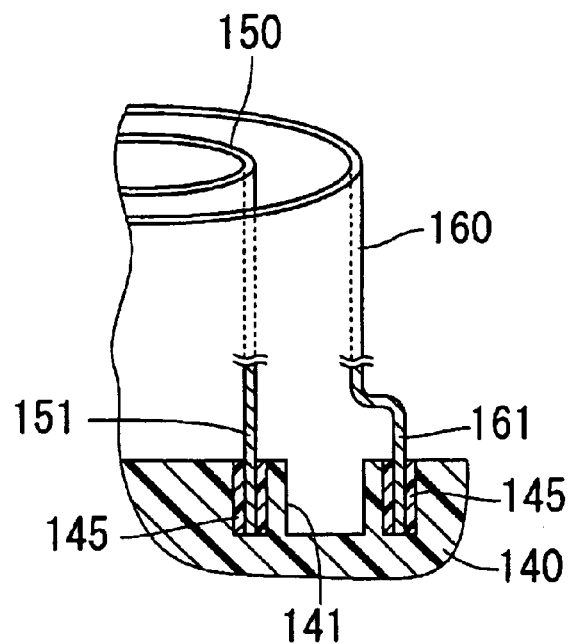
FIG. 13 is a schematic cross-sectional view showing an oil condition sensor according to the sixth embodiment of the present invention.

In the sixth embodiment shown in FIG. 13, a mounting portion 161 of a second electrode 160 is bent in the direction away from a mounting portion 151 of a first electrode 150 so that the mounting portion 161 is fixedly secured to a support member 140 at a position remoter from the mounting portion 151 compared to the fifth embodiment. Since a creepage distance of the support member 140 between the mounting portion 151 and the mounting portion 161 can be elongated more, even when a conductive foreign material which is mixed into oil, for example, is adhered to a surface of the support member 140 which is positioned between the mounting portions, it is possible to prevent the electric conduction between the mounting portion 122 and the mounting portion 132 through the foreign material. Since it is possible to prevent a leak current from flowing between the mounting portion 151 and the mounting portion 161, that is, between the electrode 150 and the electrode 160, the accuracy of detection of the potential between the electrodes can be enhanced.

(Seventh Embodiment)

Figure 14:
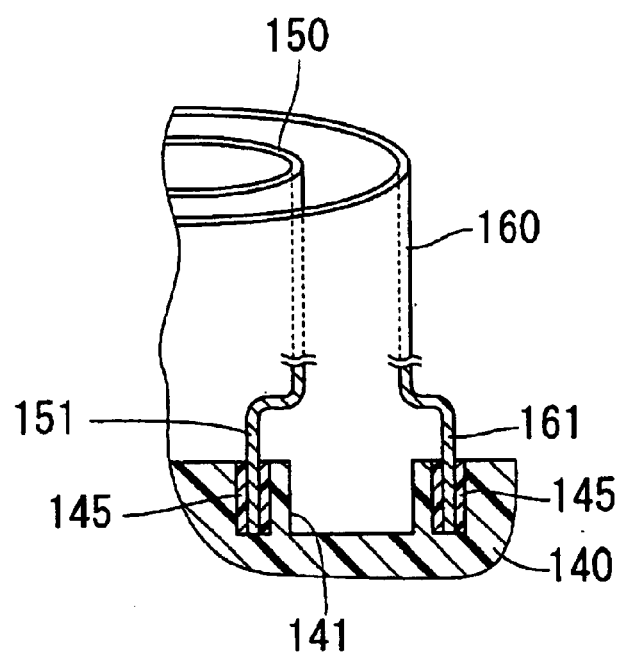
FIG. 14 is a schematic cross-sectional view showing an oil condition sensor according to the seventh embodiment of the present invention.

In the seventh embodiment shown in FIG. 14, a mounting portion 151 of a first electrode 150 and a mounting portion 161 of a second electrode 160 are respectively bent in the directions away from opposing mounting portions and are fixedly secured to a support member 140. Since a creepage distance of the support member 140 between the mounting portion 151 and the mounting portion 161 can be further elongated, it is possible to prevent a leak current from flowing between the first electrode 150 and the second electrode 160 through a surface of the support member 140.

[Eighth Embodiment]

Figure 15:
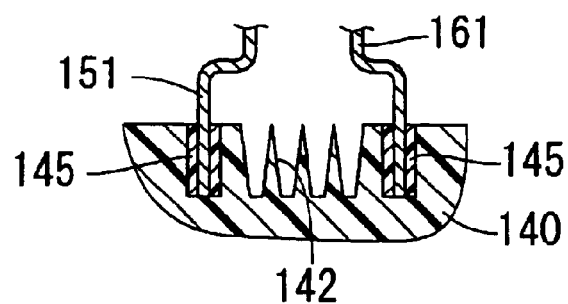
FIG. 15 is a schematic cross-sectional view showing an oil condition sensor according to the eighth embodiment of the present invention.

In the eighth embodiment shown in FIG. 15, mounting portions 151 and 161 having shapes equal to the shapes of the mounting portions 151 and 161 of the seventh embodiment are provided. On a surface of a support member 140 on which the mounting portions 151 and 161 are mounted, an uneven surface 142 having a comb-like cross section is formed between the mounting portion 151 and the mounting portion 161. Since a creepage distance of the support member 140 between the mounting portion 151 and the mounting portion 161 can be elongated, it is possible to prevent a leak current from flowing between the first electrode 150 and the second electrode 160 through the surface of the support member 140.

(Ninth Embodiment)

An oil condition sensor 210 according to the ninth embodiment of the present invention is shown in FIG. 16A to FIG. 18. Terminals 12 which are electrically connected with respective electrodes are embedded into a support member 11 formed of an insulation resin material. A cover 15 is connected to the support member 11 so as to cover an electrode structural body 220. Communication holes 15a are formed in the cover 15 such that oil can flow between the inside and the outside of the cover 15. The electrode structural body 220 is mounted on the support member 11 using an adhesive agent or the like. The electrode structural body 220 is immersed in oil filled in an oil pan or the like.

Figure 16A:
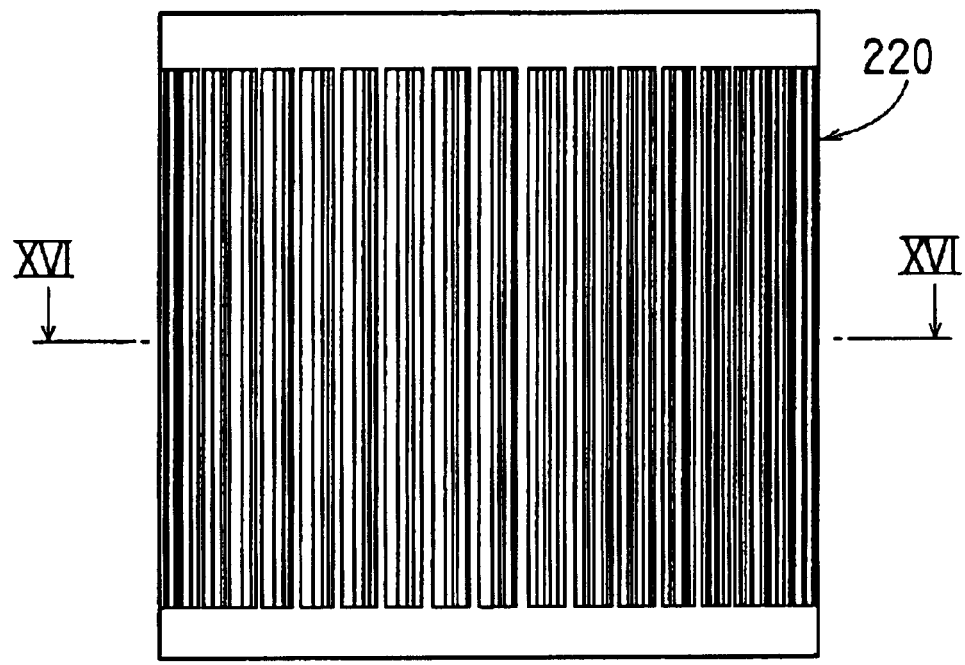
FIG. 16A is a front view showing an electrode structural body of an oil condition sensor according to the ninth embodiment of the present invention.
Figure 16B:
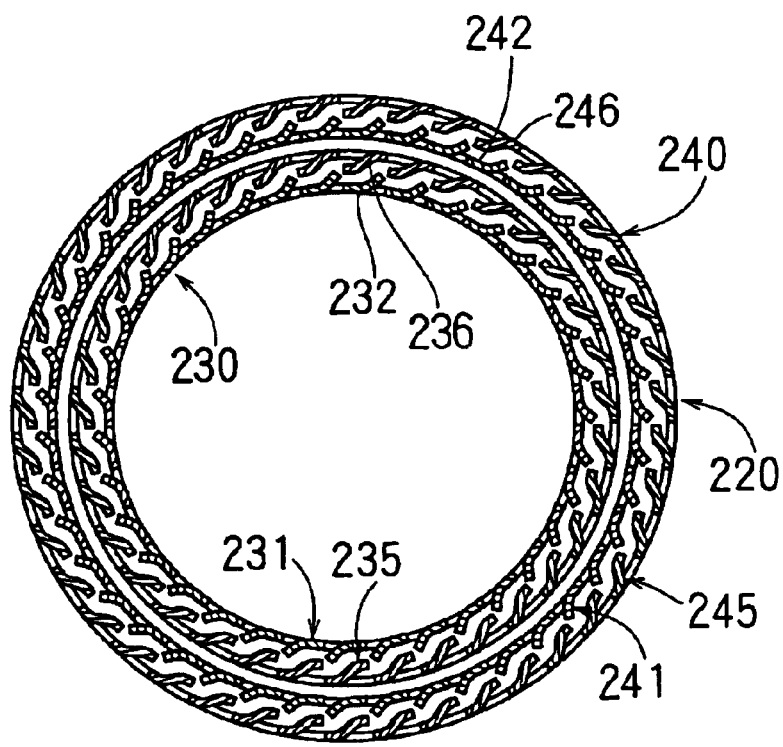
FIG. 16B is a cross-sectional view taken along a line XVI—XVI of FIG. 16A.
Figure 17:
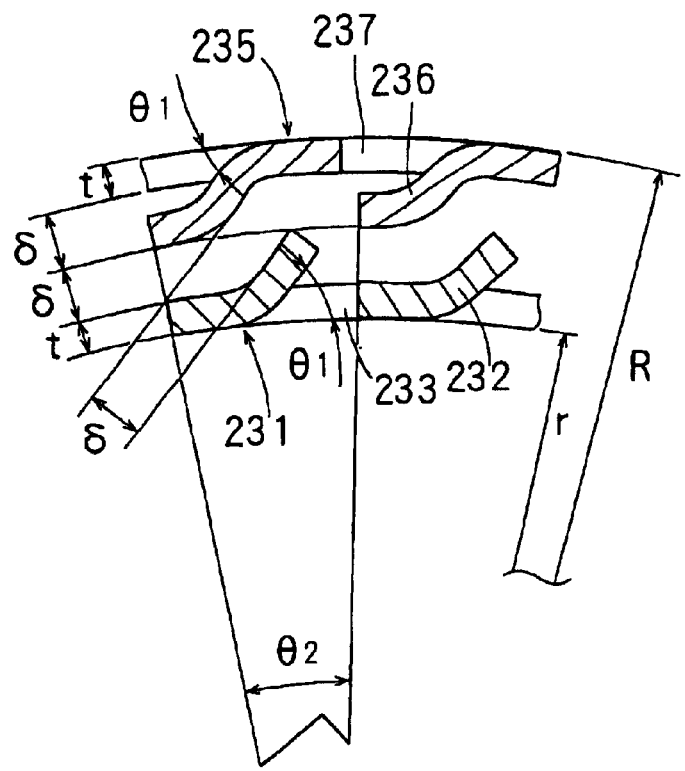
FIG. 17 is an enlarged view showing a pair of electrodes according to the ninth embodiment.
Figure 18:
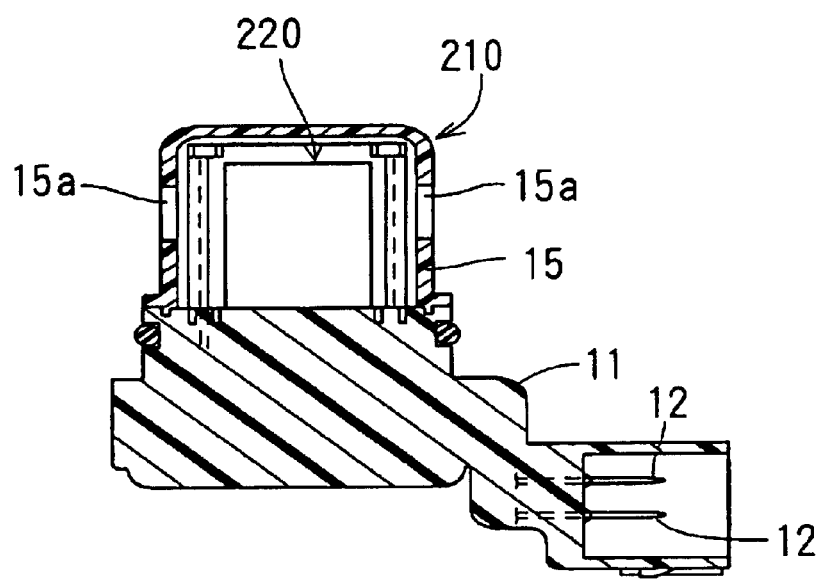
FIG. 18 is a cross-sectional view showing the oil condition sensor according to the ninth embodiment.

As shown in FIG. 16A and FIG. 16B, the electrode structural body 220 includes a pair of inner electrodes 230 having a first electrode 231 and a second electrode 235 and a pair of outer electrodes 240 which are arranged around the outer periphery of the pair of inner electrodes 230 such that the pair of outer electrodes 240 surround the pair of inner electrodes 230 coaxially. Although the pair of inner electrodes 230 and the pair of outer electrodes 240 differ with respect to their diameters, they substantially share the same shape and constitution. The pair of inner electrodes 230 are explained hereinafter mainly, wherein the explanation will be also applicable to the pair of outer electrodes 240.

The pair of inner electrodes 230 includes the first electrode 231 and the second electrode 235 which is coaxially arranged outside the first electrode 231. Both electrodes are formed in a cylindrical shape. One of these electrodes is formed of metal whose potential is not substantially changed irrespective of the PH value of oil and the other electrode is formed of metal whose potential is changed in response to the PH value of oil.

The first electrode 231 includes first fins 232 which are projected to the outside of the cylinder toward the second electrode 235 and extend in the axial direction. Between the neighboring first fins 232 and 232 in the circumferential direction, communication holes 233 which provide the communication between the inside and the outside of the cylinder of the first electrode 231 and allow the flow of oil is formed. The second electrode 235 includes second fins 236 which are projected to the inside of the cylinder toward the first electrode 231 and extend in the axial direction. Between the neighboring second fins 236 and 236 in the circumferential direction, communication holes 237 which provide the communication between the inside and the outside of the cylinder of the second electrode 235 and allow the flow of oil is formed. Since oil flows between the inside and the outside of respective electrodes through the communication holes 233 and the communication holes 237, it is possible to prevent oil from dwelling on the peripheries of both electrodes. Accordingly, the deterioration state of the whole oil can be detected with high accuracy.

The first fins 232 and the second fins 236 are formed by cutting and bending sheet-like pre-forms. The pre-forms in which respective fins are formed are rounded to form a cylindrical shape and both end portions of respective pre-forms are welded to form respective electrodes.

The number of the fins formed in the first electrode 231 is equal to the number of the fins formed in the second electrode 235 and both electrodes 231 and 235 exhibit the same bending angle θ1 of the fins with respect to the original cylindrical wall position before cutting and bending, wherein the bending angle θ1 is set to 0<θ1<π/2.

A thickness t of the first electrode 231 may be equal to or different from a thickness t of the second electrode 235. In this embodiment, the explanation is made assuming that both electrodes 231 and 235 have the same thickness. The distance δ between both electrodes including the fins are equal and are set to δ≦1 mm. Assuming the outermost diameter of the second electrode 235 as R, the inner diameter r of the first electrode 231 takes a value which can be obtained by an equation r=R−2t−2δ. An angle θ2 which one fin formed on the first electrode 231 occupies in the circumferential direction is set equal to an angle θ2 which one fin formed on the second electrode 235 occupies in the circumferential direction. Assuming the number of fins respectively formed on both electrodes as n, the angle θ2 becomes θ2=(2π/n).

Assuming the length of the cylindrical wall corresponding to the angle θ2 before forming the first fins 232 by bending the cylindrical wall of the first electrode 231 as L, the length becomes L=(2πr/n)=2π (R−2t−2δ)/n. The first fins 232 are formed by bending the cylindrical wall such that the bending angle θ1 takes a value 0<θ1<π/2 at a position which assumes one half of the length L.

Since respective fins of both electrodes are formed with bending angles of less than 90°, it is possible to prevent respective fins from approaching excessively to the opposing electrodes. Accordingly, the distance between the first electrodes 231 and the second electrodes 235 including the fins can be easily maintained at a substantially fixed value in the circumferential direction. Further, cracks hardly occur at bent corner portions.

Figure 19:
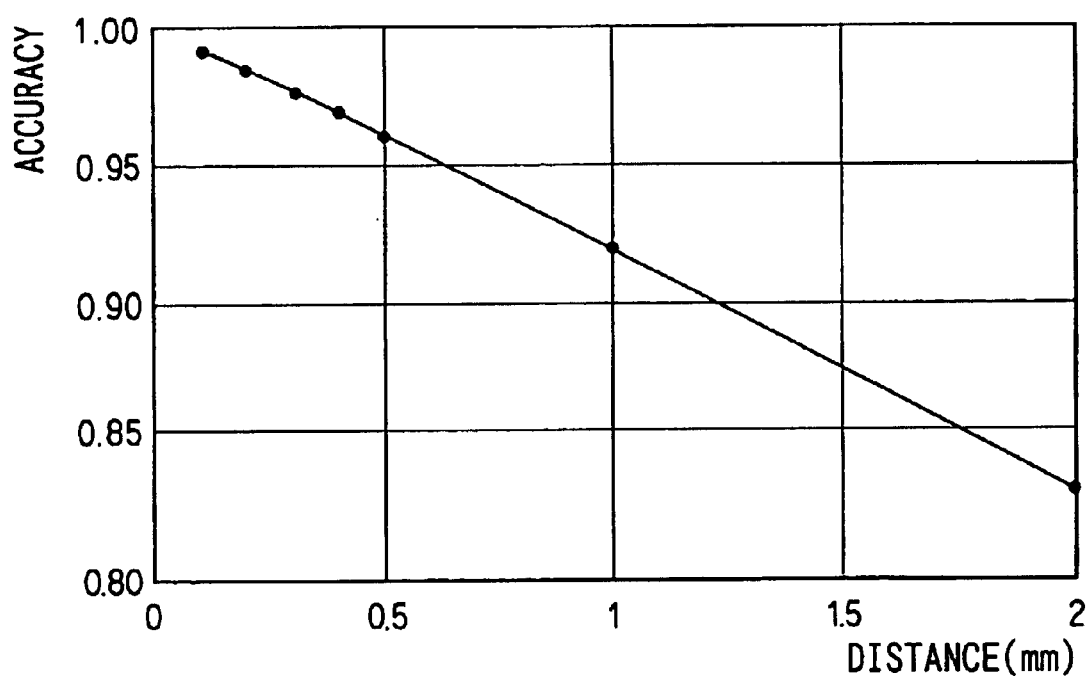
FIG. 19 is a characteristic diagram showing the relationship between the interval between electrodes and the measurement accuracy.

With respect to the voltage which is generated between the first electrode 231 and the second electrode 235 due to the deterioration of oil, the measured voltage which is actually measured from both electrodes is lowered when the resistance between the electrodes is increased. To prevent the lowering of the measured voltage for detecting the deterioration of oil with high accuracy, it is desirable to enhance the accuracy of measurement which is a ratio of the measured voltage with respect to the voltage which is generated between the electrodes. As a method for enhancing the accuracy of measurement, the reduction of the resistance between electrodes by increasing the facing areas of the electrodes or narrowing the distance between the electrodes is considered. In view of such consideration, in the ninth embodiment, the distance δ between the electrodes is set to a value in a size range which satisfies δ≦1 mm in view of a desired potential difference output and the above-mentioned both matters in terms of the formation of electrodes. As shown in FIG. 19, by making the distance δ satisfy δ≦1 mm, the accuracy of measurement is held at 90% or more. The narrower the distance between the electrodes, the accuracy of measurement is enhanced.

Further, since respective fins are formed without wasting a part of the pre-forms, the decrease of the facing areas of the electrodes can be prevented. Still further, since the communication holes 233 and 237 are formed along with the formation of the fins, oil is allowed to flow between the inside and the outside of respective cylinders of the first electrode 231 and the second electrode 235. Since oil is prevented from dwelling in the peripheries of the electrodes, the condition of oil can be detected with high accuracy.

(Tenth Embodiment)

Figure 20A:
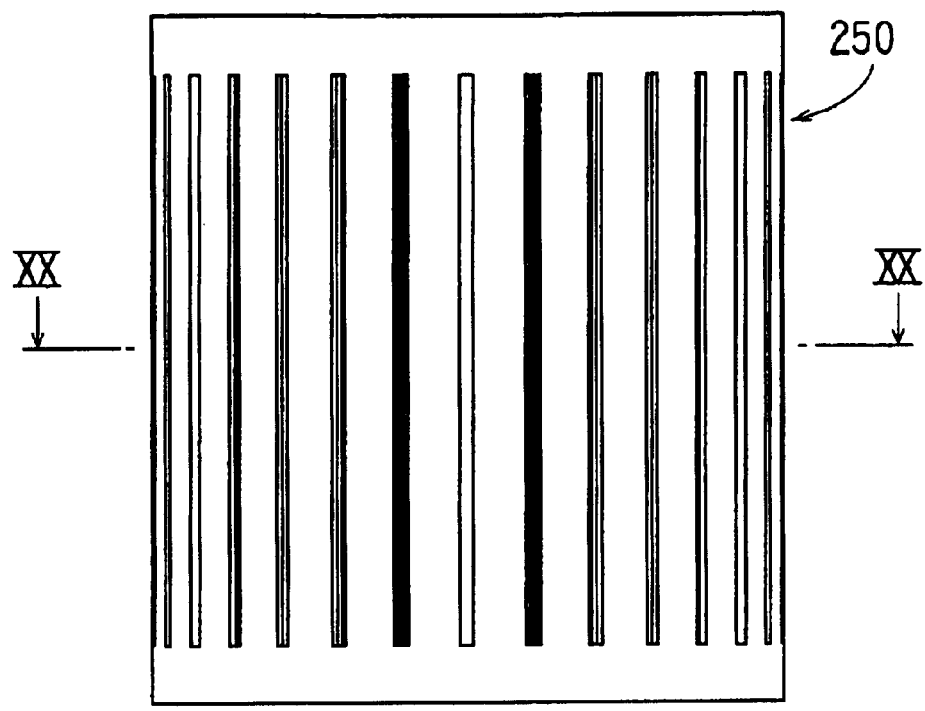
FIG. 20A is a front view showing an electrode structural body of an oil condition sensor according to the tenth embodiment of the present invention.
Figure 20B:
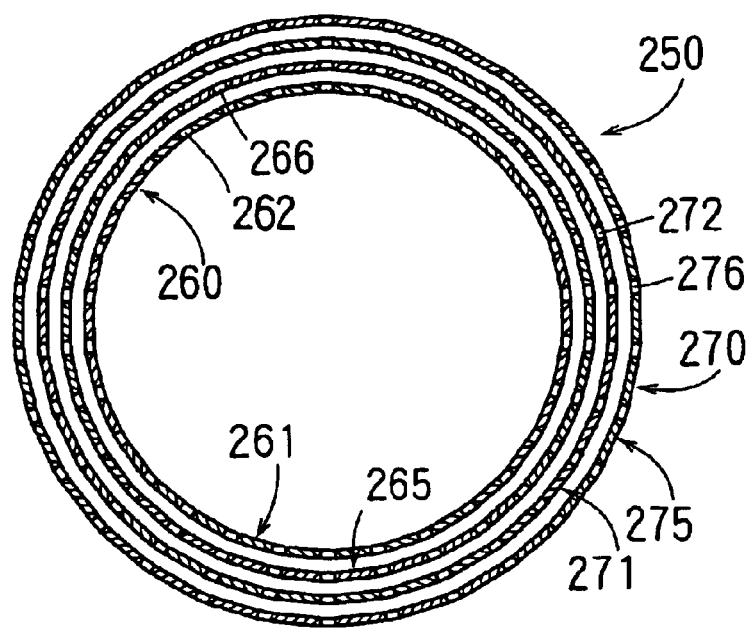
FIG. 20B is a cross-sectional view taken along a line XX—XX of FIG. 20A.

In FIG. 20A and FIG. 20B, an electrode structural body 250 includes a pair of inner electrodes 260 and a pair of outer electrodes 270 which are disposed around an outer periphery of a pair of inner electrodes 260 such that the outer electrodes 270 surround a pair of inner electrodes 260. A pair of inner electrodes 260 includes a first electrode 261 and a second electrode 265, while a pair of outer electrodes 270 includes a first electrode 271 and a second electrode 275. Respective electrodes are formed in a cylindrical shape. The diameters of the first electrode 261, the second electrode 265, the first electrode 271 and the second electrode 275 are increased in this order and they are mounted coaxially.

The electrodes are provided with slits 262, 266, 272 and 276. The slits constitute communication holes extending in the axial direction and arranged at an equal angular distance in the circumferential direction. The slits 262, 266, 272 and 276 are formed and positioned at the same circumferential positions to align radially. Oil flows between the inside and the outside of respective electrodes by passing through the slits 262, 266, 272 and 276. Since oil is prevented from dwelling in the peripheries of the electrodes, the condition of oil can be detected with high accuracy.

(Eleventh Embodiment)

Figure 21A:
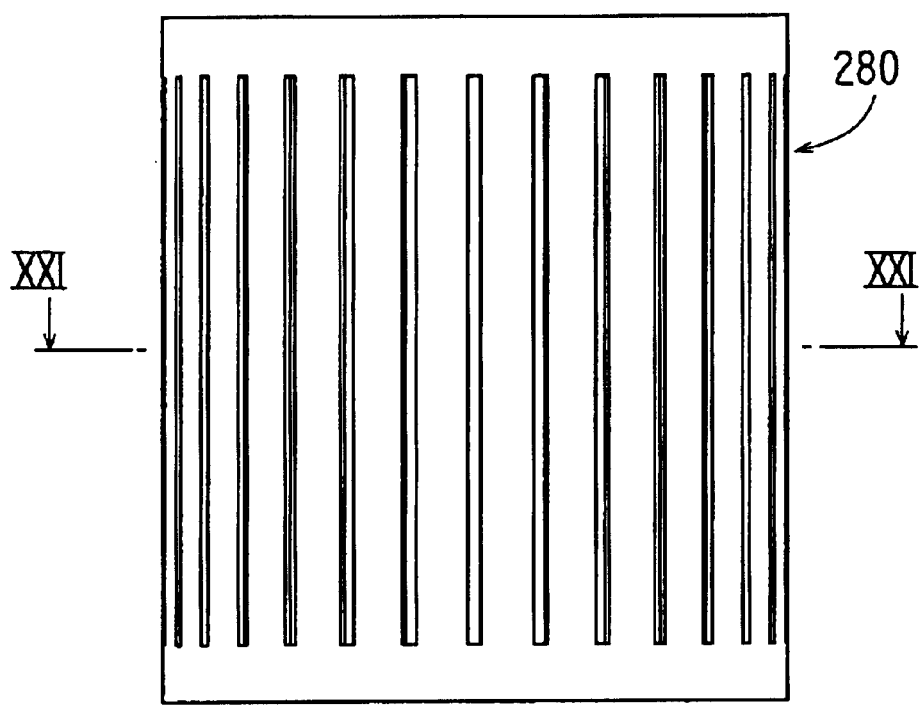
FIG. 21A is a front view showing an electrode structural body of an oil condition sensor of a modification according to the eleventh embodiment of the present invention.
Figure 21B:
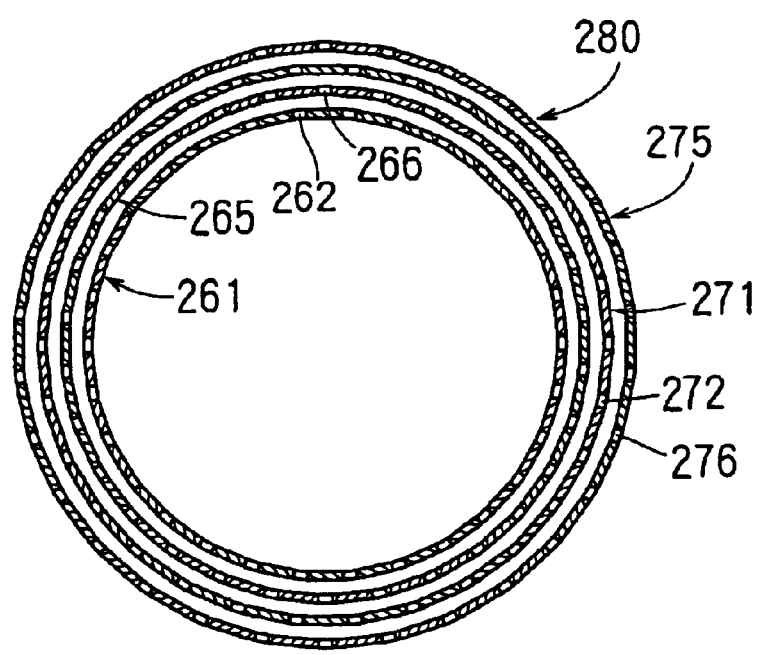
FIG. 21B is a cross-sectional view taken along a line XXI—XXI of FIG. 21A.

Respective electrodes of the tenth embodiment are not provided with projections such as fins projecting toward the as inside or the outside of the cylinder and have the same thickness in the circumferential direction. Accordingly, provided that the respective electrodes are mounted coaxially, as in the case of an electrode structural body 280 of this embodiment shown in FIG. 21A and FIG. 21B, even when the rotational positions of respective electrodes are offset or displaced from the rotational positions shown in FIG. 20B, although facing areas of the electrodes are slightly decreased, the distance between the electrodes is set equal over the circumference. Accordingly, the electrodes can be assembled easily.

(Twelfth Embodiment)

Figure 22A:
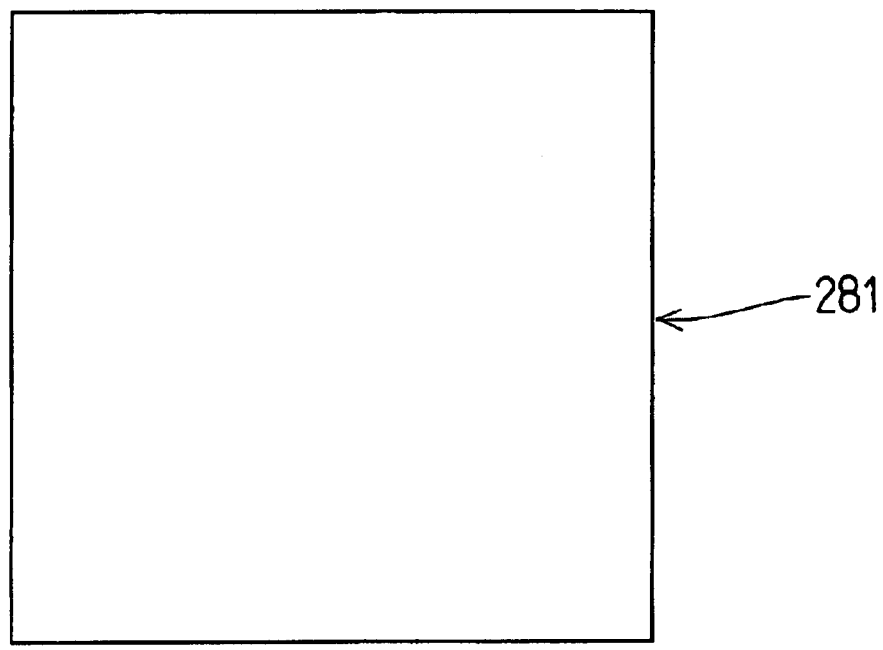
FIG. 22A is a front view showing an electrode structural body of an oil condition sensor according to the twelfth embodiment of the present invention.
Figure 22B:
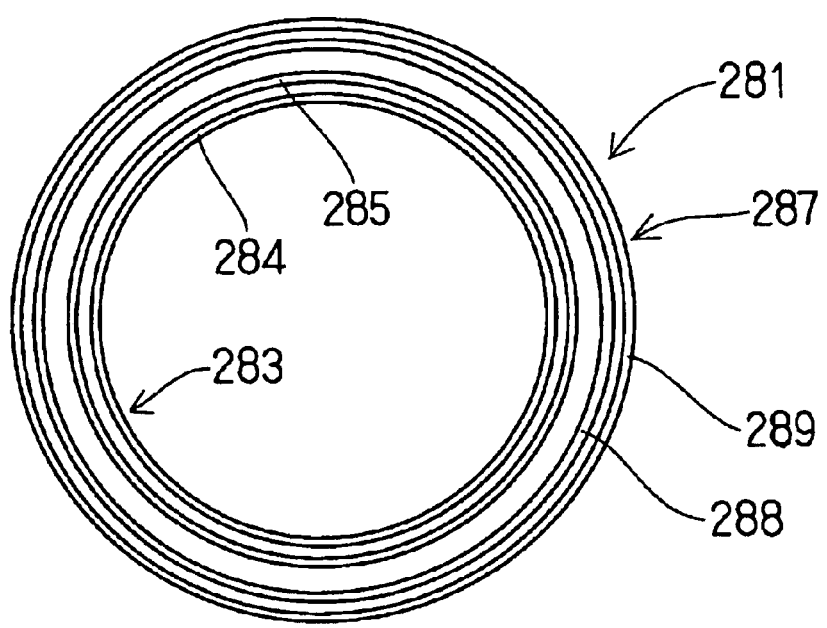
FIG. 22B is a view as viewed from the direction XXII of FIG. 22A.

In FIG. 22A and FIG. 22B, an electrode structural body 281 includes a pair of inner electrodes 283 and a pair of outer electrodes 287. A pair of inner electrodes 283 includes a first electrode 284 and a second electrode 285, while a pair of outer electrodes 287 includes a first electrode 288 and a second electrode 289. Respective electrodes are formed in a cylindrical shape. The diameters of the first electrode 284, the second electrode 285, the first electrode 288 and the second electrode 289 are increased in this order and they are mounted coaxially.

While being formed in a cylindrical shape, respective electrodes are not provided with slits similar to those of the second embodiment and hence, oil is prevented from flowing between the inside and the outside of the cylinders of respective electrodes. Further, even when the rotational positions of respective electrodes are offset or displaced, the distance between the electrodes and the facing areas of the electrodes are not changed and hence, the positioning of respective electrodes in the rotational direction is unnecessary. Accordingly, the assembling of the electrodes is facilitated.

(Thirteenth Embodiment)

Figure 23A:
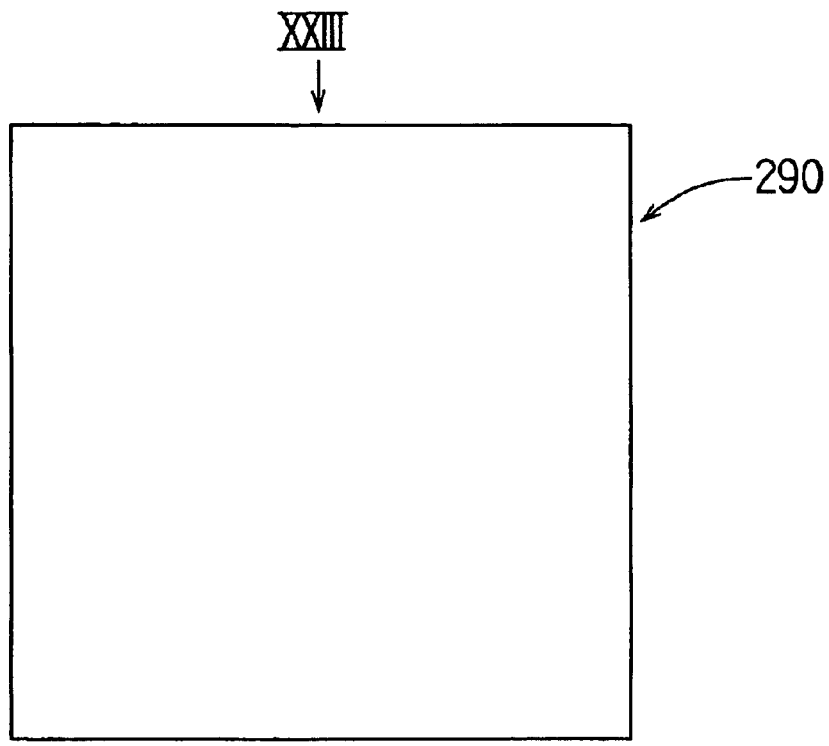
FIG. 23A is a front view showing an electrode structural body of an oil condition sensor according to the thirteenth embodiment of the present invention.
Figure 23B:
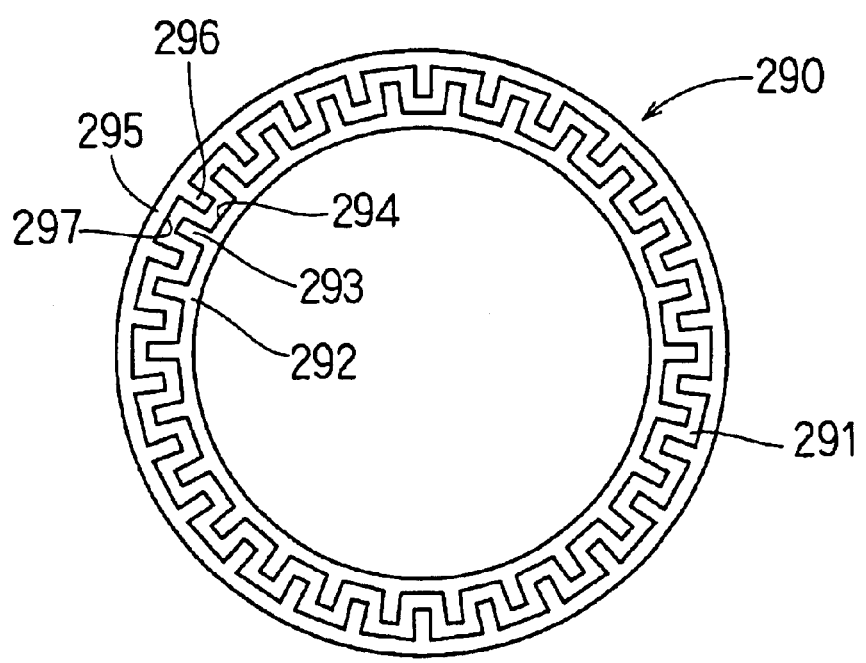
FIG. 23B is a view as viewed from the direction XXIII of FIG. 23A.

As shown in FIG. 23A and FIG. 23B, an electrode structural body 290 is comprised of a pair of electrodes having a first electrode 292 and a second electrode 295. The second electrode 295 is arranged coaxially around an outer periphery of the first electrode 292 such that the second electrode 295 surrounds the first electrode 292. Both electrodes are formed by a drawing process.

The first electrode 292 includes a plurality of projections 293 which are projected toward the outside of cylinder, that is, toward the second electrode 295, are extended in the axial direction and are arranged at an equal angular distance in the circumferential direction. The second electrode 295 includes projections 296 which are projected toward the inside of cylinder, that is, toward the first electrode 292, are extended in the axial direction and are arranged at an equal angular distance in the circumferential direction.

A distance which the first projection 293 defines with the neighboring second projections 296 which are disposed at both sides of the first projection 293 in the circumferential direction is set equal to a distance which a distal end of the first projection 293 defines with an inner bottom surface 297 disposed between circumferentially neighboring second projections 296. Further, a distance which the second projection 296 defines with the neighboring first projections 293 which are disposed at both sides of the second projection 296 in the circumferential direction is set equal to a distance which a distal end of the second projection 296 defines with an outer bottom surface 294 disposed between circumferentially neighboring first projections 293. Accordingly, the distance between the first electrode 292 and the second electrode 295 is substantially fixed over the circumference including the distal ends of respective projections.

Figure 24A:
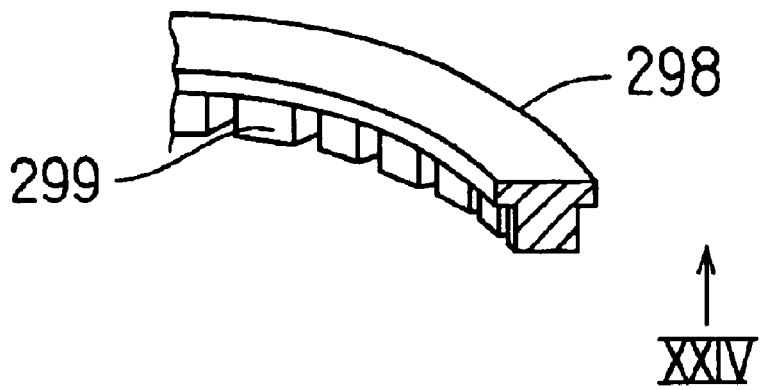
FIG. 24A is a perspective view with a part in cross section showing a contact prevention member according to the thirteenth embodiment of the present invention.
Figure 24B:
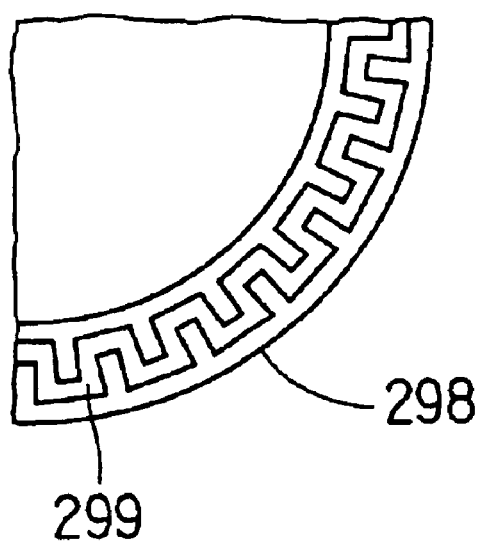
FIG. 24B is a view as viewed from the direction XXIV of FIG. 24A.
Figure 25:
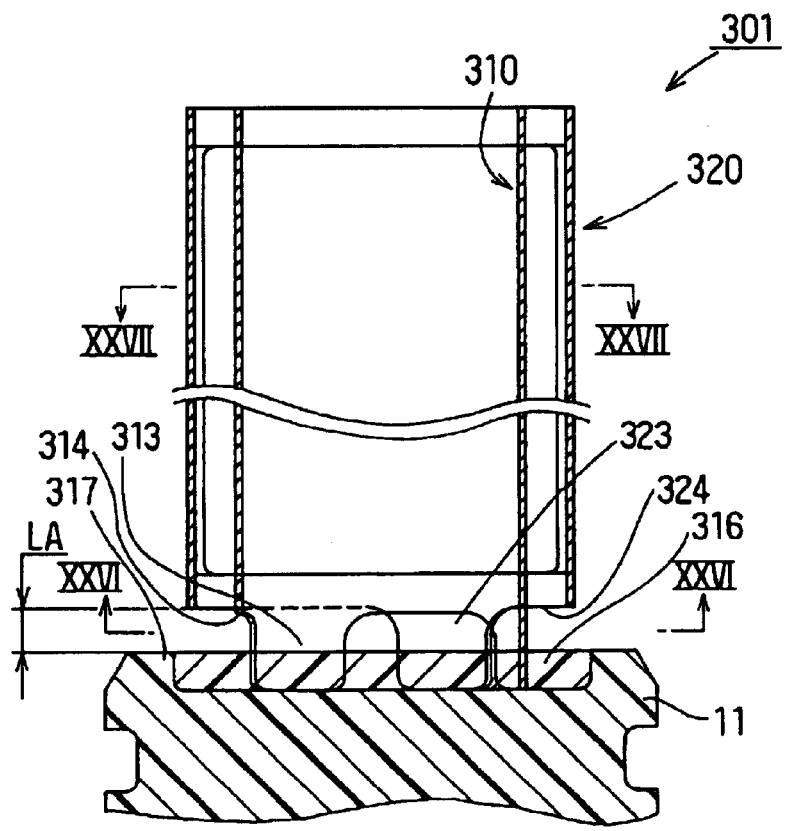
FIG. 25 is a cross-sectional view showing a portion of an oil condition sensor according to the fourteenth embodiment of the present invention.
Figure 26:
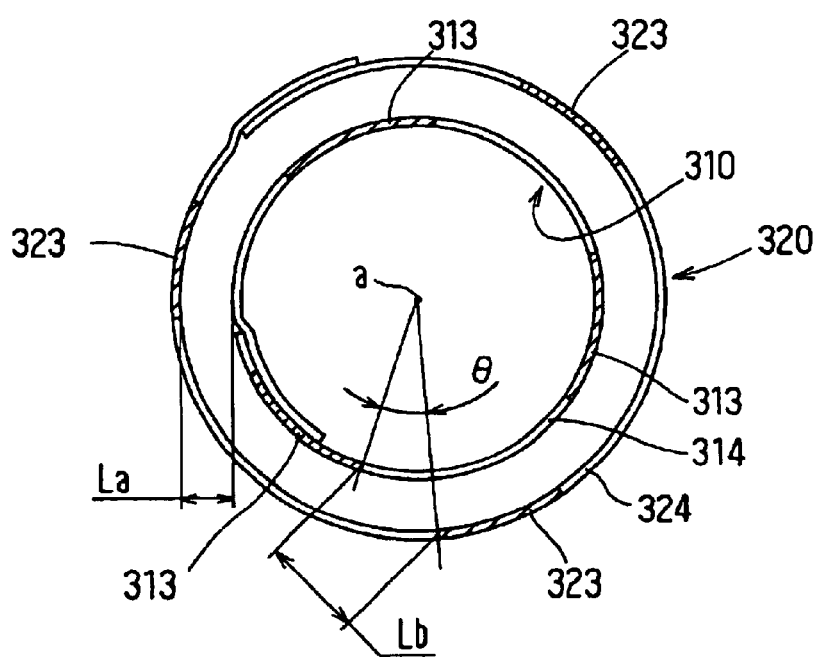
FIG. 26 is a cross-sectional view taken along a line XXVI—XXVI shown in FIG. 25.
Figure 27:
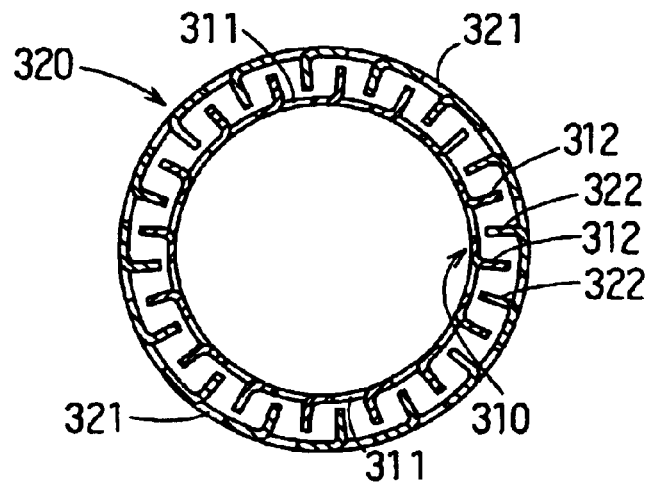
FIG. 27 is a cross-sectional view taken along a line XXVII—XXVII shown in FIG. 25.
Figure 28:
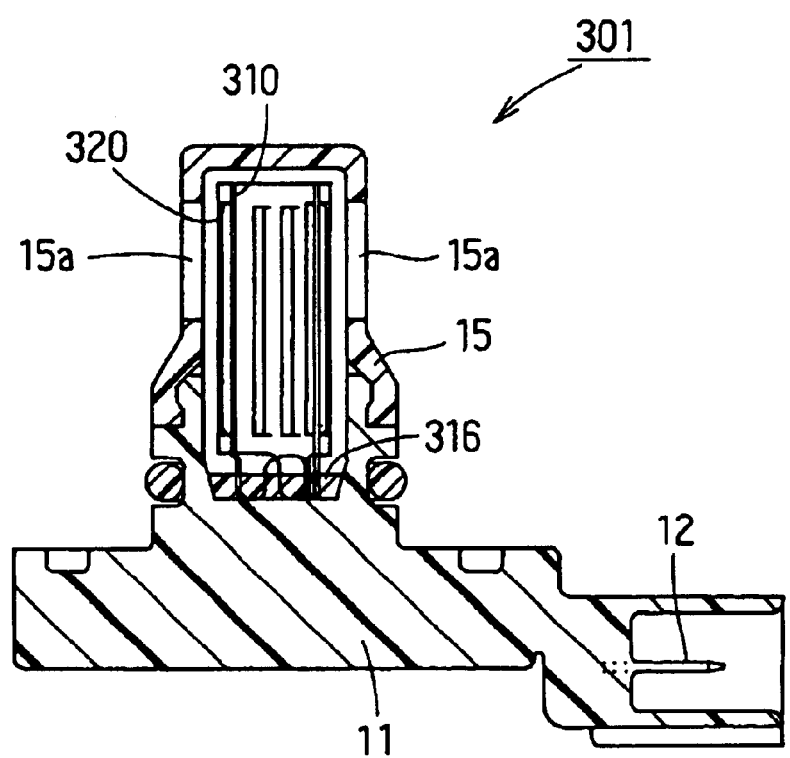
FIG. 28 is a cross-sectional view showing an oil condition sensor according to the fourteenth embodiment of the present invention.

Into a space 291 which is formed between both ends of both electrodes at a distal end side having no support member 11 (see FIG. 3A), projections 299 of a contact prevention member 298 shown in FIG. 24A are fitted. The contact prevention member 298 is formed of insulation material such as PPS (polyphenylene sulfide). The projections 299 of the contact prevention member 298 are formed to match the shape of the space 291. The contact prevention member 298 prevents both electrodes from being deformed due to the vibration transmitted to both electrodes from a vehicle or the like thus preventing both electrodes being electrically communicated due to the deformation. Accordingly, it is possible to prevent the malfunction of the operation of an oil condition sensor.

In place of adopting the constitution which fits the contact prevention member 298 into the space 291, end portions of both electrodes may be immersed into molten insulation resin material and thereafter the insulation resin material is hardened by solidifying so that the contact of both electrodes can be prevented due to the hardened insulation resin material.

The contact prevention member 298 can be also applicable to other embodiments. The member 298 prevents end portions of the electrodes from coming into contact with each other due to the deformation.

In the above-mentioned embodiment, since the distance between the electrodes is substantially fixed over the circumference, the distribution of current density between electrodes becomes uniform so that the resistance between electrodes can be reduced. Since the accuracy of measurement is enhanced along with the reduction of the resistance between electrodes, the condition of oil can be detected with high accuracy.

Further, since respective electrodes are formed in a cylindrical shape, each electrode is formed of a single part. Since the number of parts can be reduced, the assembling is facilitated and the oil condition sensor can be miniaturized. Further, by extending the axial length of each electrode, the facing areas of electrodes can be easily increased. Still further, since each electrode is formed in a cylindrical shape, it is possible to ensure the space in which an oil level sensor which detects an oil level can be installed in the inside of the innermost electrode. Accordingly, the detection of the condition of oil and the detection of an oil level can be performed using the single oil condition sensor.

(Fourteenth Embodiment)

As shown in FIG. 25 to FIG. 28, an oil condition sensor 301 is comprised of an electrode portion and a support portion.

A first electrode 310 and a second electrode 320 are formed in a cylindrical shape. Both electrodes 310 and 320 are substantially coaxially arranged by making the diameters of both cylindrical electrodes 310 and 320 different from each other such that the second electrode 320 is disposed outside the first electrode 310. One of both electrodes 310 and 320 is formed of metal whose potential is not substantially changed irrespective of the PH value which indicates the condition of oil, while the other electrode is formed of metal whose potential is changed in response to the PH value.

The first electrode 310 and the second electrode 320 are respectively provided with fins 312 and 322 which are extended in the radially outwardly direction and in the radially inwardly direction and are arranged adjacent to each other without coming into contact with each other. Communications holes 311 and 321 are respectively formed between the fins located on the same side, e.g. 312 and 312, or 322 and 322. These communication holes 311 and 321 prevent oil from dwelling in a space defined between both electrodes 310 and 320.

Terminals 12 which are electrically connected to the electrodes 310 and 320 are embedded in the support member 11. A cover 15 is jointed to the support member 11 so as to cover the electrodes 310 and 320. Communication holes 15a that allow oil to flow between the inside and the outside of the cover 15 are formed in the cover 15.

First and second projections 313 and 323 having a convex shape which are extended in the downward direction are formed on portions of cylindrical peripheral walls of both electrodes 310 and 320. In this embodiment, three pieces of first and second projections 313 and 323 are formed for each electrode 310 and 320. Portions (lowermost end portions) of the first and second projections.313 and 323 are fixedly secured to the support member 11 made of electrically insulating resin using an adhesive agent 316. A distance of given size (LA) is formed between lower end portions 314 and 324 of the cylindrical peripheral walls of both electrodes 310 and 320 and a surface 317 on which both electrodes are supported (hereinafter referred to as "support connection surface").

The first and second projections 313 and 323 are arranged such that they are displaced from each other in the circumferential direction. That is, an angle θ is made between a line which connects a cylindrical center point "a" of both electrodes 310 and 320 and an end portion of the first projection 313 and a line which connects the cylindrical center point "a" of both electrodes 310 and 320 and an end portion of the second projection 323. Accordingly, a creepage distance Lb between the first and second projections 313 and 323 on the support connection surface 317 can be elongated. Here, the creepage distance Lb has a relationship La<Lb with respect to a creepage distance La between both electrodes 310 and 320 in the radial direction.

The creepage distance Lb between the first and second projections 313 and 323 is ensured at any one of three sets of portions between the first and second projections 313 and 323. Accordingly, the range of the lower end in the circumferential direction in which the edge portions 314 and 324 are formed can be set larger than the range of the lower end in the circumferential direction in which the projections 313 and 323 are formed.

According to this embodiment, the creepage distance Lb between the electrodes can be elongated without increasing the diameters of the cylindrical walls of both electrodes 310 and 320. Due to this elongation of the creepage distance Lb between both electrodes, the lowering of the insulation resistance which may occur when conductive foreign material adheres to an outer surface of the support member 11 can be suppressed so that the sensor output can be made stable. This advantageous effect becomes more apparent when an oil condition sensor 300 is mounted on an oil pan in an erected state. That is, the miniaturization of the oil condition sensor 300 and the enhancement of the detection accuracy can be achieved simultaneously.

(Fifteenth Embodiment)

Figure 29:
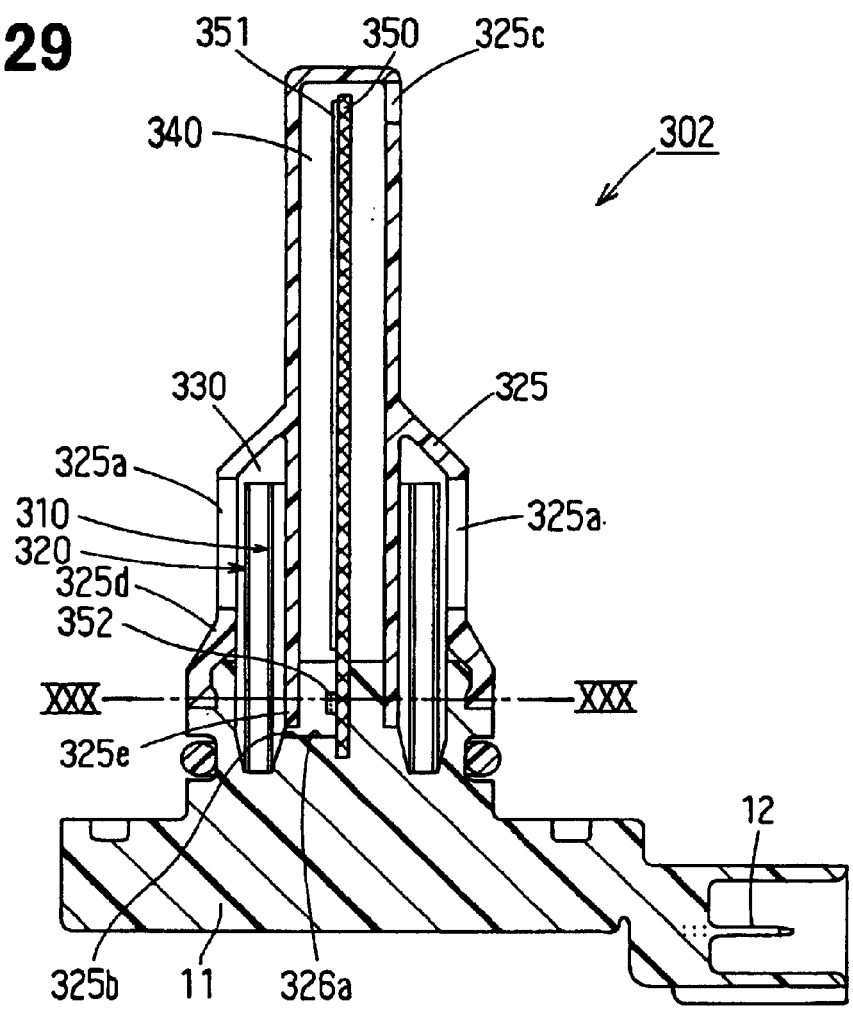
FIG. 29 is a cross-sectional view showing an oil condition sensor according to the fifteenth embodiment of the present invention.
Figure 30:
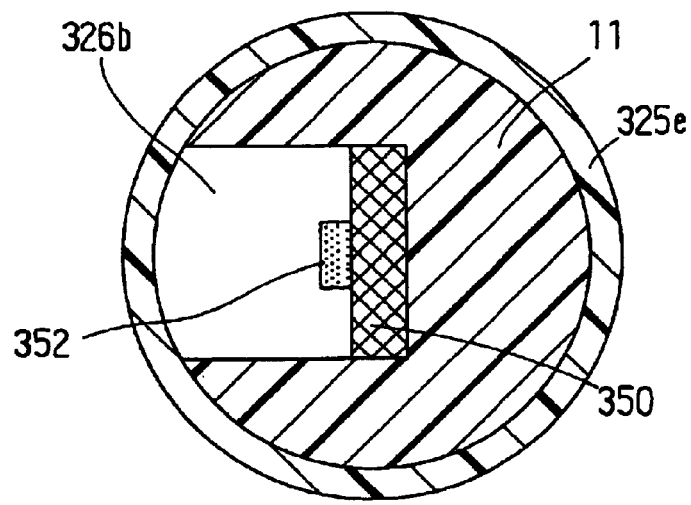
FIG. 30 is a cross-sectional view taken along a line XXX—XXX shown in FIG. 29.
Figure 31:
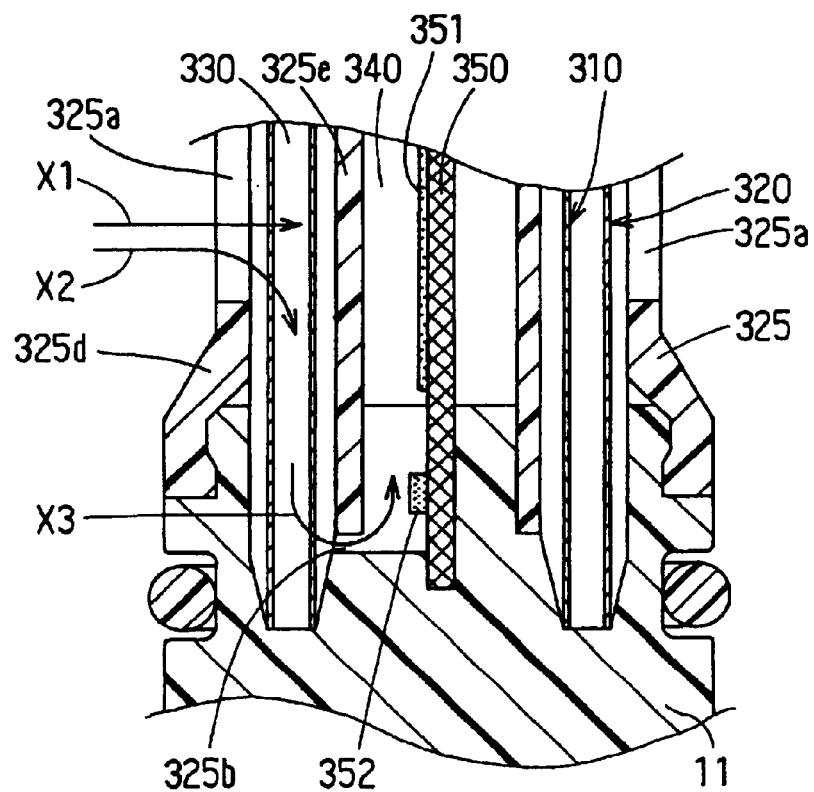
FIG. 31 is a partially enlarged cross-sectional view around a periphery of support member shown in FIG. 29.

An oil condition sensor 302 shown in FIG. 29 to FIG. 31 is provided with first and second electrodes 310 and 320 and an oil level sensor 351 which can detect an oil level. Here, the oil level sensor 351 also has a function of detecting a liquid surface level of oil so that an oil level can be calculated by taking a shape of the oil pan into consideration.

A first measurement chamber 330 which arranges the electrodes 310 and 320 therein and a second measurement chamber 340 which arranges the oil level sensor 351 therein are formed separately by partitioning. The oil condition sensor 300 includes a cover 325 which is connected to the support member 326 and covers an condition sensor and the oil level sensor 351 and defines the first and second measurement chambers 330 and 340. The annular first measurement chamber 330 is arranged outside the columnar second measurement chamber 340.

First hole portions 325a are formed in a first wall portion 325d which forms the first measurement chamber 330 so that oil accommodated in the oil pan is introduced into the first measurement chamber 330 through the first hole portions 325a. Second hole portions 325b are formed in a second wall portion 325e which forms the second measurement chamber 340 so that oil in the inside of the first measurement chamber 330 is introduced into the second measurement chamber 340 through the second hole portions 325b.

A transverse cross section of a first opening which is disposed approximately perpendicular to the flow (direction) X1 of oil in the first hole portion 325a is formed larger than a transverse cross section of a second opening which is disposed approximately perpendicular to the flow (direction) X3 of oil in the second hole portion 325b. With respect to the second hole portion, the size of the cross section of the second opening is adjusted such that the change speed of the liquid surface level of oil accommodated in the second measurement chamber becomes slower than the change speed of the liquid surface level of oil accommodated in the oil pan when the oil pan is tilted.

Further, the second hole portions 325b are formed at a position below the first hole portions 325a, that is, at a position in the vicinity of an upper end surface 326a of the support member. In an upper end portion of the cylindrical cover 325, a hole 325c which allows the smooth inflow of oil into the second measurement chamber 340 and the smooth outflow of oil from the second measurement chamber 340 is formed. A notched portion 326b is formed in the support member 326 thus forming an oil passage to the inside of the second measurement chamber 340.

The oil flows which pass through the first hole portions 325a comprise the oil flow X1 which advances straight and the oil flow X2 which is bent and is directed to the second hole portion 325b. By allowing a portion of the oil flow X2 to pass through the second hole portions 325b which are formed smaller than the first hole portions 325b, the oil flow X3 whose oil flow rate to the second measurement chamber 340 is limited is obtained. Accordingly, even when a transitional fluctuation occurs with respect to the oil level in the inside of the oil pan, the oil level in the second measurement chamber 340 can be made stable by preventing the oil level in the second measurement chamber 340 from following the fluctuation of oil level in the inside of the oil pan whereby the detection of oil can be performed accurately. That is, the detection performance of the oil level sensor 351 can be enhanced.

The oil level sensor 351 is formed by mounting a detection body formed in an elongated strip shape along a substrate 350, wherein the detection body is capable of taking an output value which corresponds to the ratio of a portion thereof immersed in oil. The substrate 350 has one end thereof fixedly secured to a portion of the support member 11. Further, a temperature sensor 352 which can detect the temperature of oil is mounted on the substrate 350. The temperature sensor 352 is disposed at a position in the vicinity of the second hole portion 325b in the inside of the second measurement chamber 340 and at a position where the oil flow X3 which flows into the second measurement chamber 340 through the second hole portion 325b impinges on the temperature sensor 352.

Accordingly, the temperature sensor 352 can detect both temperatures in the first and second measurement chambers 330 and 340. That is, signals from one temperature sensor 352 are commonly used for temperature correction of output values of both of the condition sensor and the oil level sensor 351 and hence, the oil condition sensor 302 can be miniaturized. Further, the temperature sensor 352 is mounted on the substrate 350 on which the oil level sensor 351 is also mounted and hence, it is unnecessary to separately ensure a mounting space for disposing the temperature sensor 352 whereby the oil condition sensor 302 can be miniaturized.

(Sixteenth Embodiment)

Figure 32:
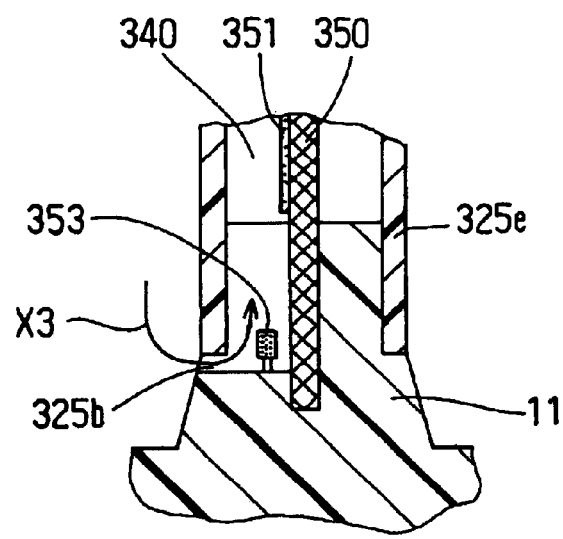
FIG. 32 is a partial cross-sectional view showing an oil condition sensor of the sixteenth embodiment of the present invention.

In this embodiment, as shown in FIG. 32, a temperature sensor is directly supported on and fixedly secured to a portion of a support member 11 without being mounted on a substrate 350. Here, the temperature sensor 353 which is directly supported on and fixedly secured to the support member 11 is disposed at a position where an oil flow X3 to a second measurement chamber 40 impinges on the temperature sensor 353.

Figure 33:
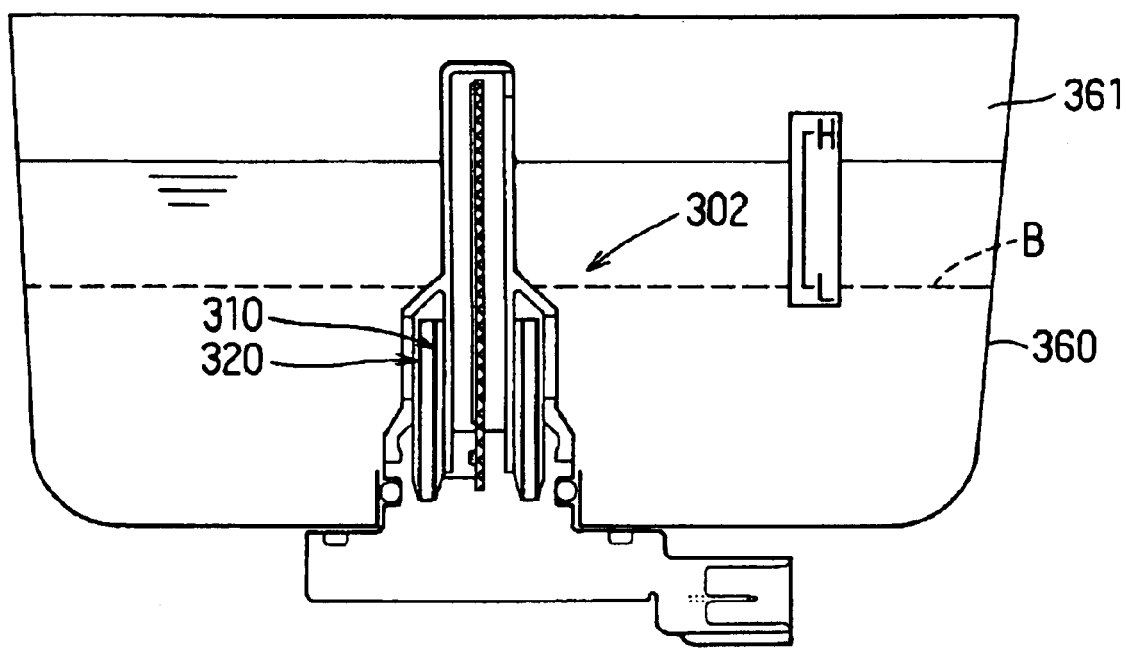
FIG. 33 is a cross-sectional view showing a state in which the oil condition sensor shown in FIG. 29 is mounted on an oil pan.
Figure 34:
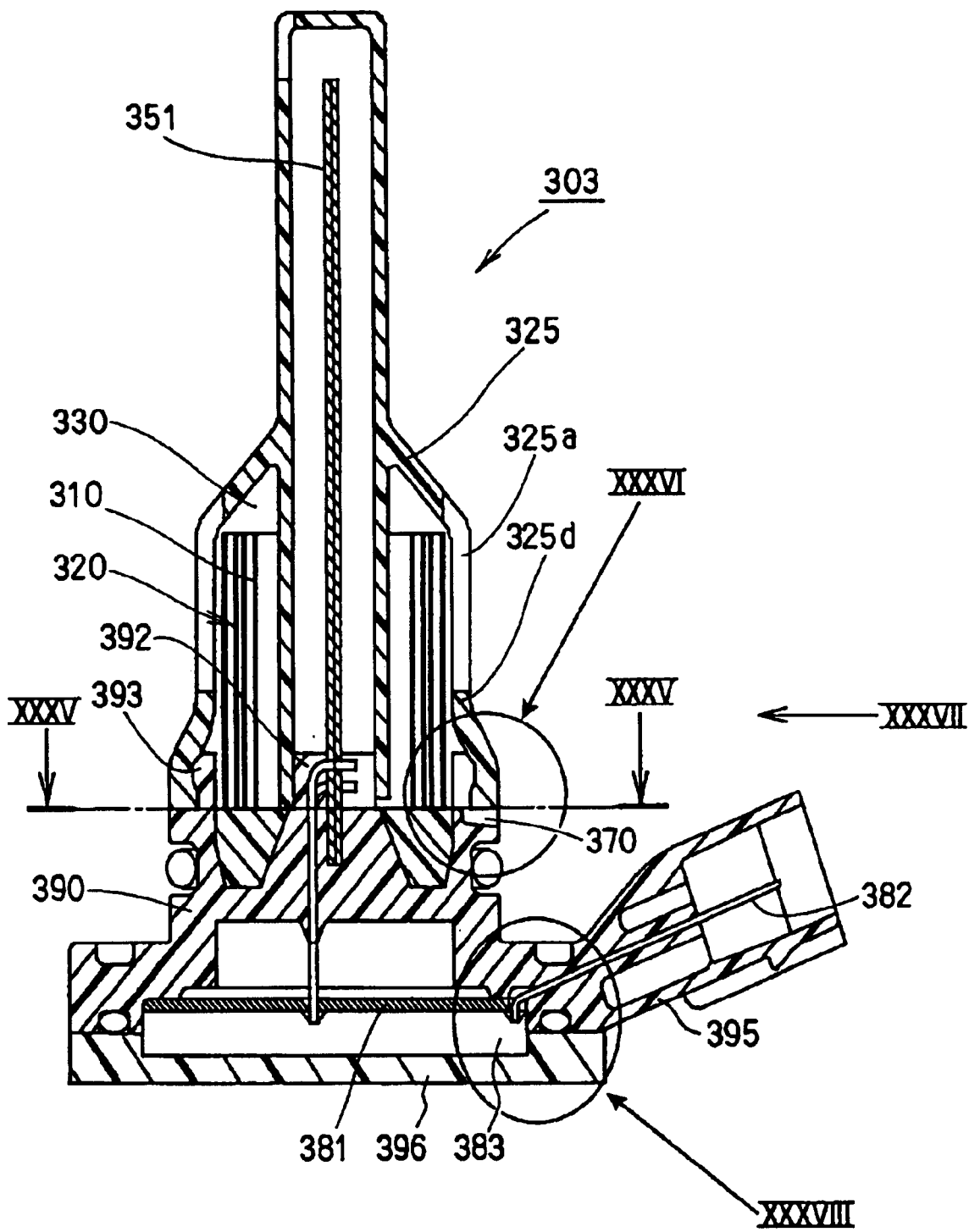
FIG. 34 is a cross-sectional view showing an oil condition sensor according to the seventeenth embodiment of the present invention.
Figure 35:
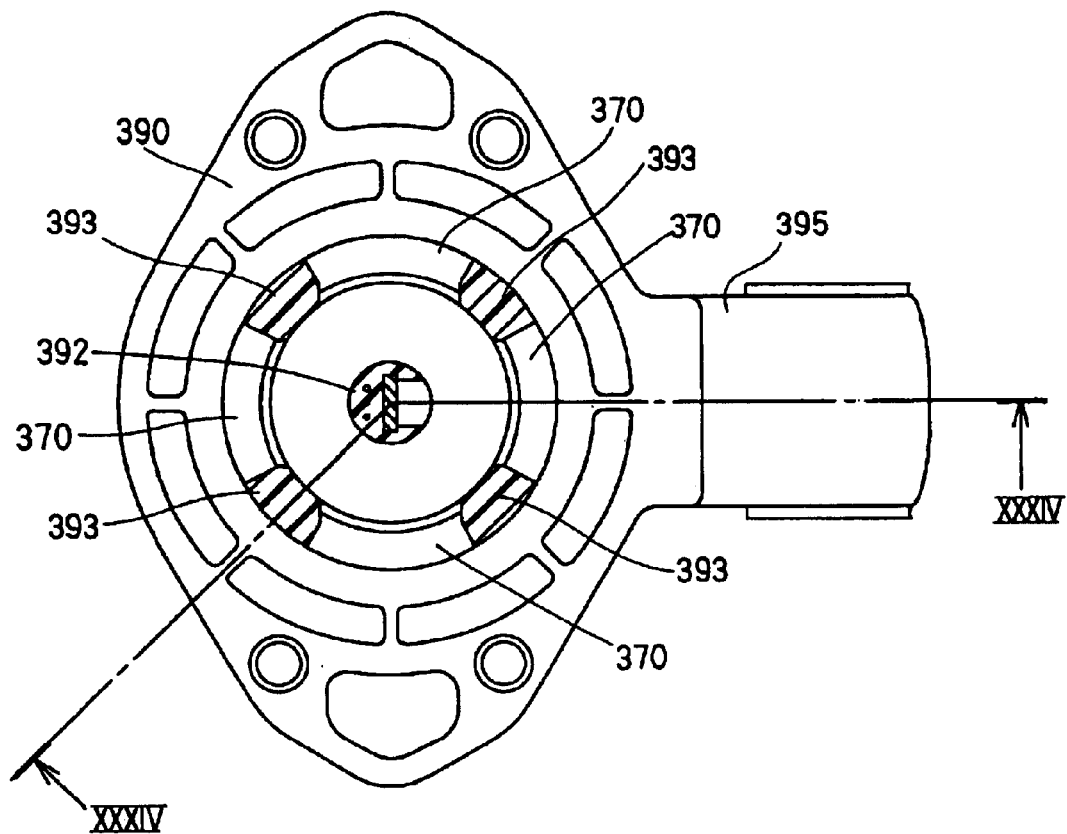
FIG. 35 is a cross-sectional view taken along a line XXXV—XXXV shown in FIG. 34.

The oil condition sensor of the fifteenth embodiment and the sixteenth embodiment is mounted in the inside of an oil tank 361 as shown in FIG. 33. The first and second electrodes 310 and 320 are arranged such that both electrodes 310 and 320 have the whole structural bodies thereof immersed in oil when oil is filled with an oil level set at a predetermined oil lower limit level B in the oil tank 361. Since the whole of the first and second electrodes 310 and 320 are immersed in oil when oil is filled with oil level set at the predetermined oil lower limit level B, the potential difference between both electrodes 310 and 320 can be made stable so that the accuracy of detection of oil condition can be enhanced.

(Seventeenth Embodiment)

An oil condition sensor 303 of the seventeenth embodiment of the present invention is explained in conjunction with FIG. 34 to FIG. 40.

Figure 36:
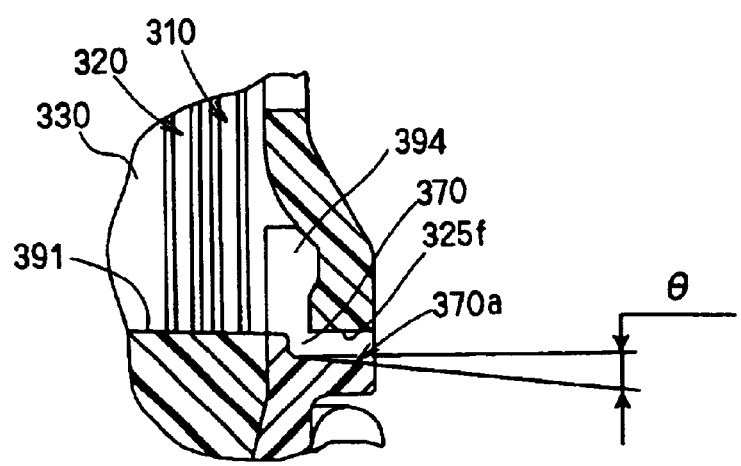
FIG. 36 is a detailed view of a XXXVI part in FIG. 34.
Figure 37:
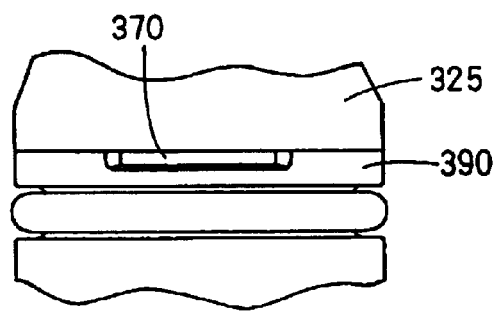
FIG. 37 is a partial view of the oil condition sensor shown in FIG. 34 as viewed from an arrow direction of XXXVII.

In a first wall portion 325d of the oil condition sensor 303, an oil inflow/outflow portion 370 which enables an inflow of oil into a first measurement chamber 330 or an outflow of oil from the first measurement chamber 330 is formed such that the oil inflow/outflow portion 370 is extended in the radially outward direction of a support connection surface 391, of a support member 390 for first and second electrodes 310 and 320. The oil inflow/outflow portion 370 is disposed at a position slightly below the support connection surface 391. A downward surface which forms an opening portion defines an inclination portion 370a which is inclined downwardly from the inside to the outside of a first measurement chamber 330. In FIG. 36, the inclination portion 370a having an angle θ is shown. Further, the oil inflow/outflow portions 370 are formed in plural places which are distributed in the circumferential direction of the first wall portion 325d. For example, the oil inflow/outflow portions 370 are arranged at four places at an approximately equal distance in the circumferential direction.

The support member 390 includes a columnar body 392 and an annular body 393. The columnar body 392 is projected from a body portion of the support member 390 and is formed in a columnar shape so as to support an oil level sensor 351. The annular body 393 is approximately coaxially formed with the columnar body 392. The annular body 393 is projected from the body portion of the support member 390 and is formed in an annular shape. The annular body 393 is provided for connecting a cover 325 and the support member 390. In this embodiment, a lower end portion of the cover 325 and the annular body 393 are engaged with each other by a snap fitting.

Further, the annular body 393 includes a notched portion 394 at a portion thereof. The notched portion 394 forms an opening portion having an open end at an upper part thereof. The opening portion constitutes a portion of the oil inflow/outflow portion 370. The oil inflow/outflow portion 370 is formed in the periphery of a joint portion where the cover 325 and the support member 390 are jointed. The oil input/output portion 370 is defined by a lower end surface 325f of the cover 325, the notched D portion 394 and a groove portion formed by the inclination portion 370a. The first wall portion 325d is formed of the cover 325 and the annular body 393. The oil inflow/outflow portion 370 may be formed either in the cover 325 or in the support member 390 in a single form.

FIG. 36 shows the detail of the inclination portion 370a which is disposed at a lower surface forming an opening portion of the oil inflow/outflow portion 370. The inclination angle θ of the inclination portion 370a is set to an angle not less than 0° such that a foreign material introduced into the oil inflow/outflow portion 370 can be easily discharged to the outside along the inclination portion 370a thus suppressing the dwelling of the foreign material in the oil inflow/outflow portion 370. In this embodiment, the inclination angle θ is set to approximately 10°. Here, in place of forming the inclination portion 370a on the whole surface disposed at the lower portion of the opening portion of the oil inflow/outflow portion 370, the inclination portion 370a may be formed at a portion of the surface disposed at the lower portion of the opening portion of the oil inflow/outflow portion 370.

When oil flows in or out through the oil inflow/outflow portion 370, since the oil inflow/outflow portion 370 is formed on the support connection surface 391 in the radial direction, oil flows while coming into contact with the support connection surface 391. Due to this oil flow action, it is possible to prevent the foreign material from being stuck on the periphery of the support connection surface 391. Accordingly, the reduction of the insulation resistance between the first and second electrodes 310 and 320 which is caused by the stuck foreign material can be prevented.

Since the oil inflow/outflow portions 370 are formed in plural places which are distributed in the circumferential direction, the stuck foreign material is liable to be discharged.

Figure 38:
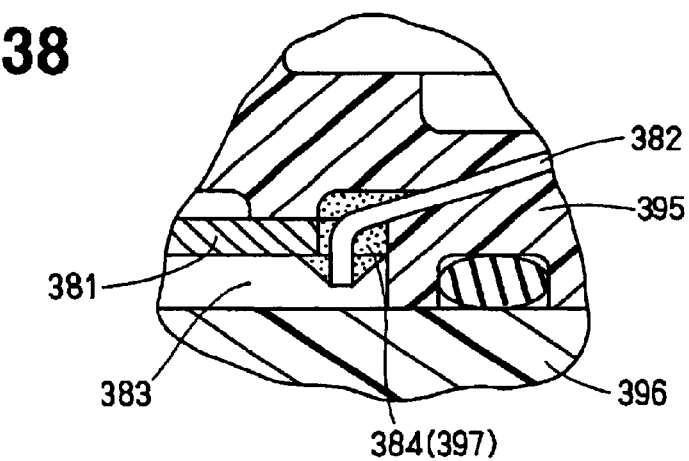
FIG. 38 is a detailed view of a part XXXVIII shown in FIG. 34.

FIG. 38 is a detailed view of a part XXXVIII of an oil condition sensor 303. A recessed portion is formed in a lower portion of the support member 390 and a circuit board 381 is accommodated in the recessed portion. A signal processing circuit is mounted on the circuit board 381 and the sensor 351 and respective electrodes 310, 320 are connected to the signal processing circuit. The support member 390 is provided with a connector portion 395 for performing the transmission of electric signals with the outside. A terminal 382 is held in the connector portion 395. One end of the terminal 382 is connected to the circuit board 381 so that signals of respective sensors are outputted. The recessed portion which accommodates the circuit board 381 is covered and sealed with a cover 396 such that a chamber 383 is defined. A projection of the terminal 382 at the chamber 383 side is provided with a sealing member 384. A sealing member holding portion 397 having a recessed shape corresponding to the projecting position of the terminal 382 is provided at the chamber 383 side of the connector portion 395.

To facilitate the connection with the circuit board 381, the terminal 382 is bent and thereafter is inserted into the connector portion 395 from the chamber 383 side. Then, sealing member 81 is attached to the sealing member holding portion 397. With the provision of the sealing member 384, the intrusion of a foreign material (water or the like) can be prevented. The bent terminal 382 prevents the withdrawal thereof from the outside thus stabilizing the mutual holding of the terminal 382 and the connector portion 395.

As the sealing member 384, a moisture proof gel or a resin adhesive agent or the like can be used. Since the sealing member 384 is disposed at the inner side of the connector portion 395, a behavior to damage the sealing member 384 does not affect the inner side of the connector portion 395 so that the attachment of the sealing member 384 is maintained in a stable manner. Further, since the sealing member holding portion 397 is formed in a recessed shape, this brings about an advantageous effect that the sealing member 384 is held in a stable manner.

Figure 40:
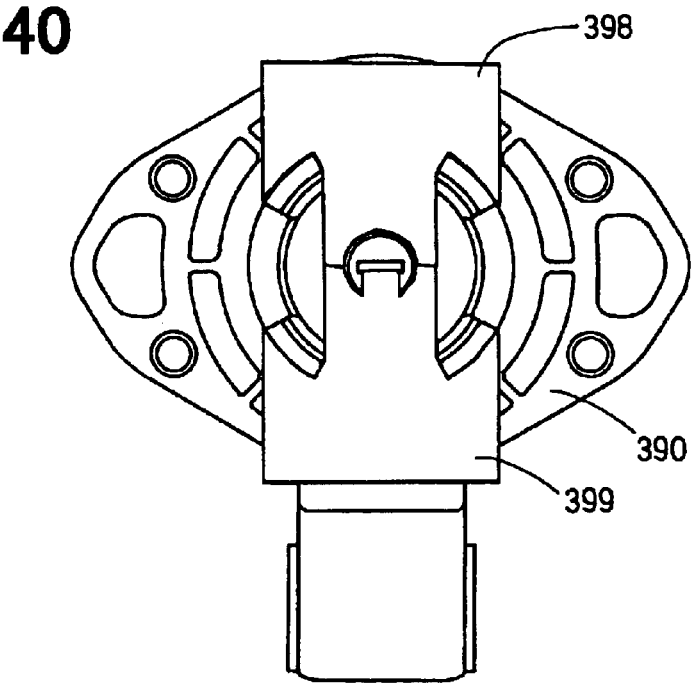
FIG. 40 is an explanatory view showing a state in which a portion of the support member is formed by molding using the mold shown in FIG. 39.
Figure 39:
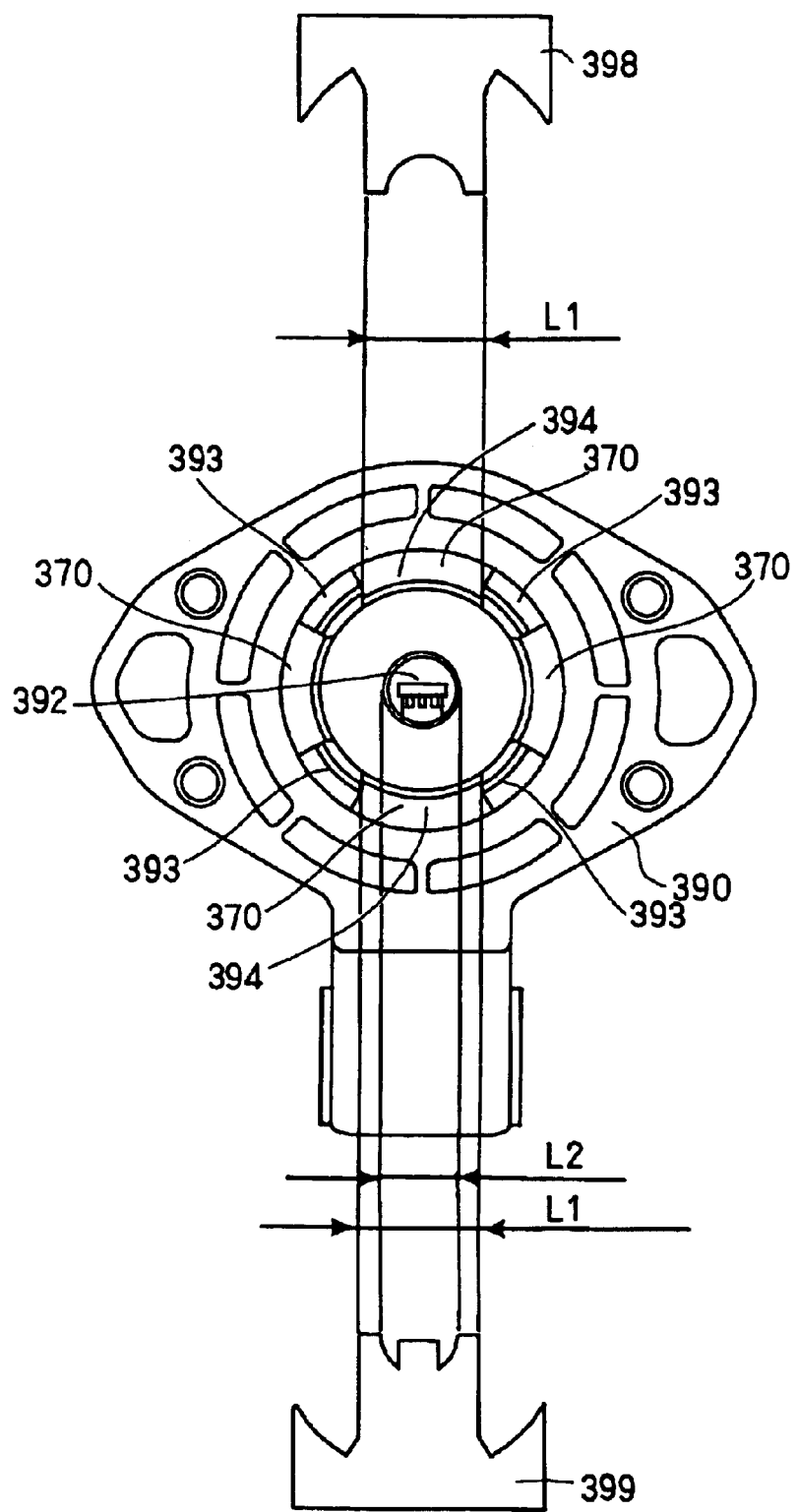
FIG. 39 is an explanatory view showing a portion of a mold and a support member formed by molding using such a mold.

Then, a molding process of the support member 390 is explained in conjunction with FIG. 39 and FIG. 40. FIG. 39 shows the relationship between molds 398 and 399 and the supporting member 390 and FIG. 40 is an explanatory view showing the molded state.

The size relationship between an opening width size L1 of the opening portions 394 of the annular body 393 and a diameter size L2 of the columnar body 392 is set to L1>L2. By providing the opening portions 394 to at least two positions in a straight line such that the opening portions 394 face the columnar body 392 in an opposed manner, the withdrawing direction of the columnar body 392 and the molds 398 and 399 which form the annular body 393 is ensured so that the columnar body 392 and the annular body 393 are integrally formed as the support member 390.

The oil inflow/outflow portion 370 may be provided only at one place. In this case, by suitably selecting the shape and the size of the opening of the oil inflow/outflow portion, it is possible to effectively suppress the stacking of a foreign material on the support connection surface 391.

(Eighteenth Embodiment)

Figure 41:
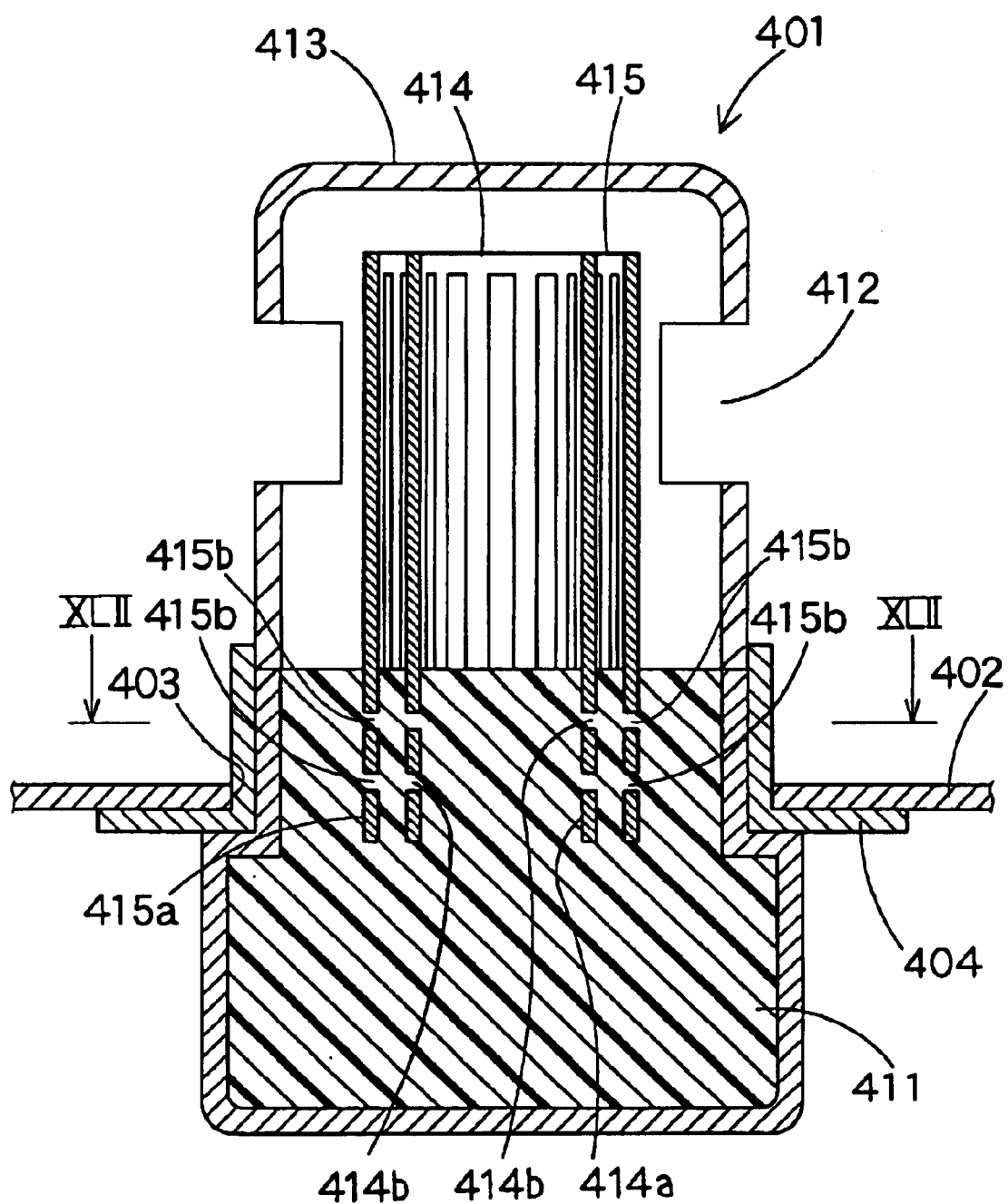
FIG. 41 is a cross-sectional constitutional view of an oil condition sensor according to the eighteenth embodiment of the present invention.
Figure 42:
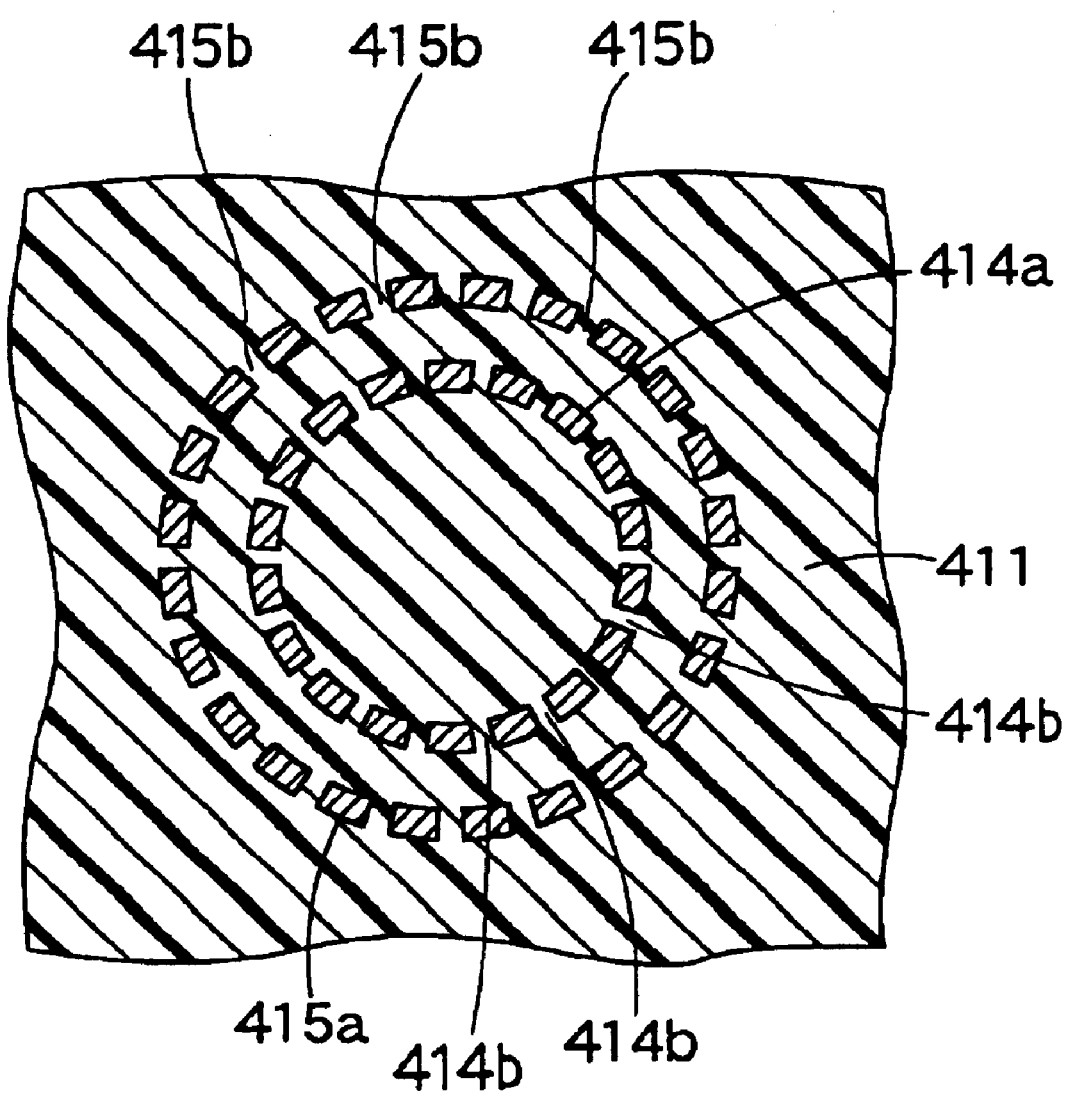
FIG. 42 is a cross-sectional view taken along a line XLII—XLII shown in FIG. 41.

As shown in FIG. 41, an oil condition sensor 401 is mounted in a mounting hole 403 formed in an oil pan 402 by way of a bracket 404. The oil condition sensor 401 includes an electrode holding portion 411 made of thermoplastic resin having the insulating ability and an approximately cylindrical cover body 413 having an oil intake port 412. Further, the oil condition sensor 401 is provided with a pair of electrodes 414 and 415, wherein a pair of electrodes 414 and 415 have respective supporting portions 414a and 415a thereof embedded in the inside of the electrode holding portion 411. As shown in FIG. 41 and FIG. 42, the supporting portions 414a, 415a of respective electrodes 414 and 415 are provided with a plurality of electrode fixing holes 414b and 415b so that the electrodes 414 and 415 are fixed to the electrode holding portion 411 by filling the thermoplastic resin in respective electrode fixing holes 414b, 415b. Here, the shape of the electrode fixing holes 414b, 415b may be either a quadrangular shape or a circular shape. When the shape of the electrode fixing holes 414b, 415b is a perfect circle, for example, the diameter thereof is set to approximately 1 mm. Further, although not shown in the drawings, respective supporting portions 414a, 415a are electrically connected to terminals by way of wiring. A pair of electrodes 414 and 415 are constituted of a cage-shaped inner-lace electrode 414 and a cage-shaped outer-lace electrode 415 which are arranged concentrically. The inner-lace electrode 414 constitutes a reference electrode formed of a metal electrode made of lead or the like, for example, and the outer-lace electrode 415 constitutes a conductive solid electrode formed of a conductor made of stainless steel having an oxide film. As a reverse case, the inner-lace electrode 414 may be constituted of a conductive solid electrode and the outer-lace electrode 415 may be constituted of a reference electrode.

Figure 43:
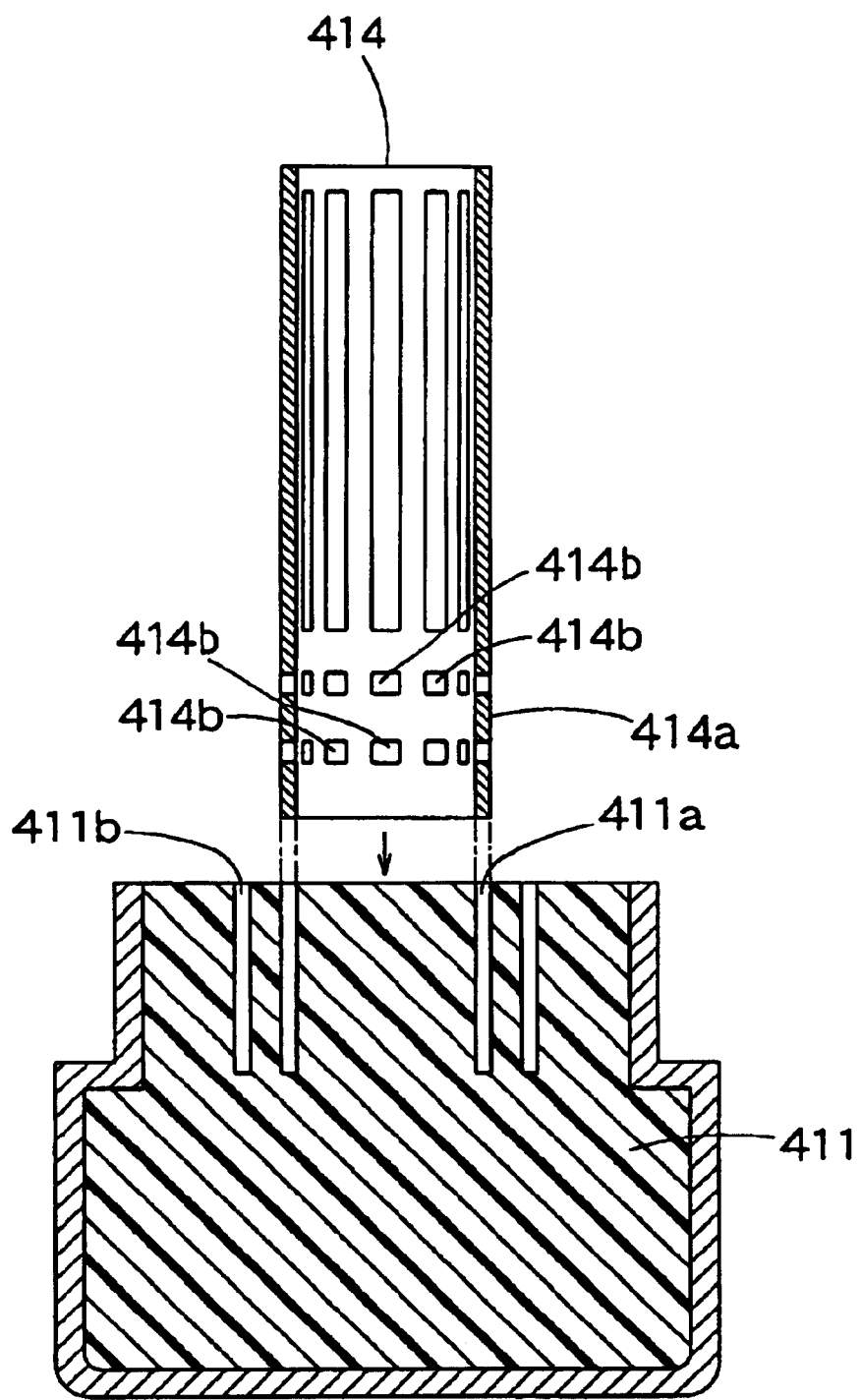
FIG. 43 is a cross-sectional view for explaining the electrode fixing process.
Figure 44:
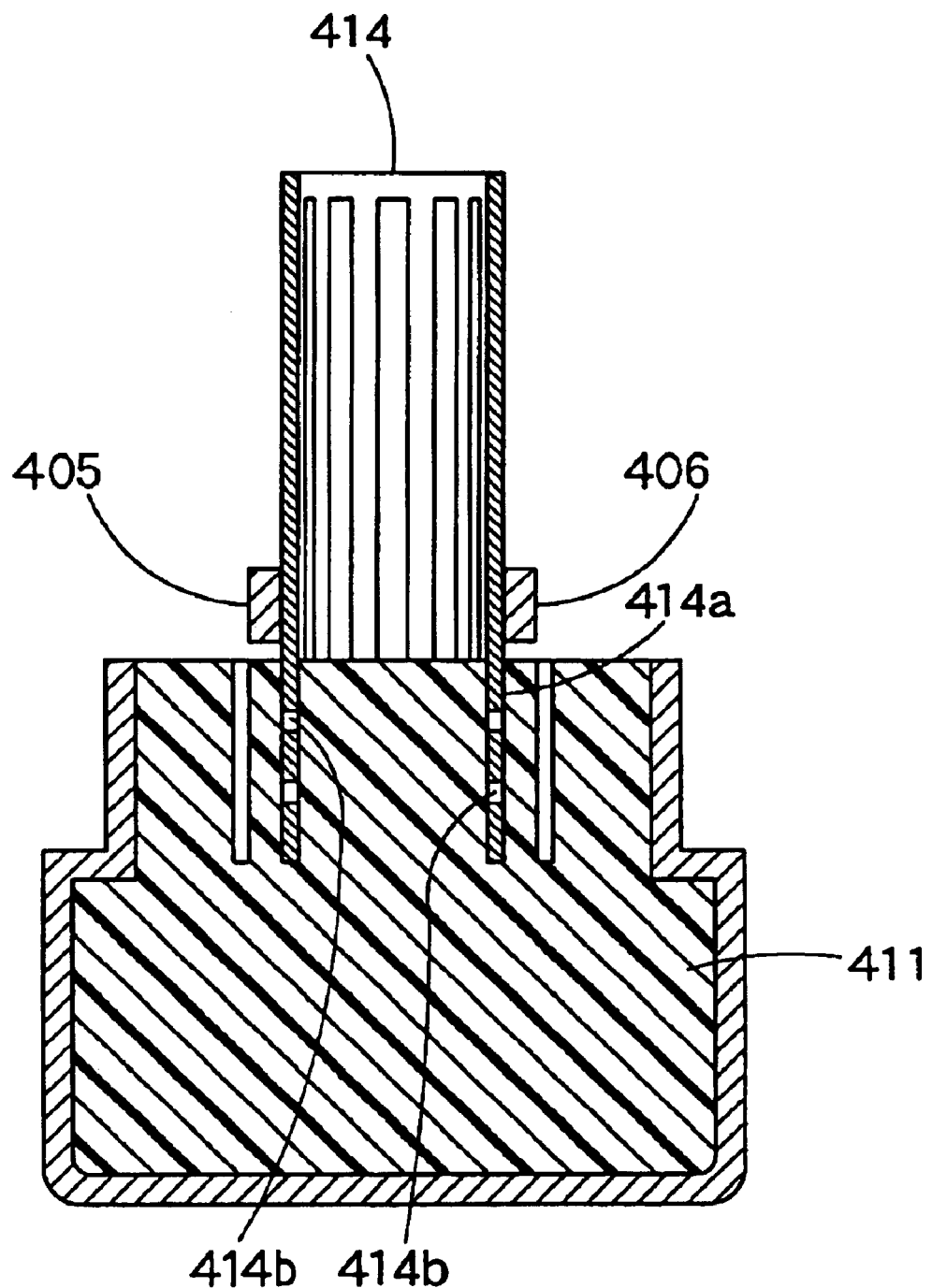
FIG. 44 is a cross-sectional view for also explaining the electrode fixing process.

Then, a method for fixing the electrodes 414 and 415 to the electrode holding portion 411 in the manufacturing process of the oil condition sensor 401 is explained in conjunction with FIG. 43 and FIG. 44.

First of all, as shown in FIG. 43, a large number of electrode fixing holds 414b are preliminarily formed in the supporting portion 414a of the inner-lace electrode 414 (although not shown in FIG. 43, a large number of electrode fixing holes 415b are also preliminarily formed in the supporting portion 415a of the outer-lace electrode 415). On the other hand, receiving portions 411a, 411b which receive respective supporting portions 414a, 415a of the inner-lace electrode 414 and the outer-lace electrode 415 are preliminarily formed in the electrode holding portion 411. In FIG. 43, the receiving portions 411a, 411b are formed of two annular grooves having different diameters.

Subsequently, as shown in FIG. 44, the supporting portions 414a, 415a of the inner-lace electrode 414 and the outer-lace electrode 415 are inserted into the receiving portions 411a, 411b.

Then, a pair of heating electrodes 405 and 406 are brought into contact with an upper portion of the supporting portion 414a of the inner-lace electrode 414 and the supporting portion 414a is heated at a temperature of 200° C. to 300° C. with electricity by applying a given voltage between the electrodes 405 and 406. When the supporting portion 414a is heated by supplying electricity, the thermoplastic resin in the vicinity of the supporting portion 414a melts and flows in respective electrode fixing holes 414b.

Thereafter, the supply of electricity is stopped so as to harden the molten thermoplastic resin.

The inner-lace electrode 414 which is fixed to the electrode holding portion 411 by exercising such electrode fixing method can exhibit an anchoring effect when the thermoplastic resin is filled in respective electrode fixing holes 414b formed in the supporting portion 414a thereof so that the inner-lace electrode 414 is firmly bonded to and held by the electrode holding portion 411.

Here, the outer-lace electrode 415 can be also fixed to the electrode holding portion 411 using a method similar to the above-mentioned method for fixing the inner-lace electrode 414.

According to this embodiment, these electrodes can be firmly fixed to the electrode holding portion without using an adhesive agent.

(Nineteenth Embodiment)

Figure 45:
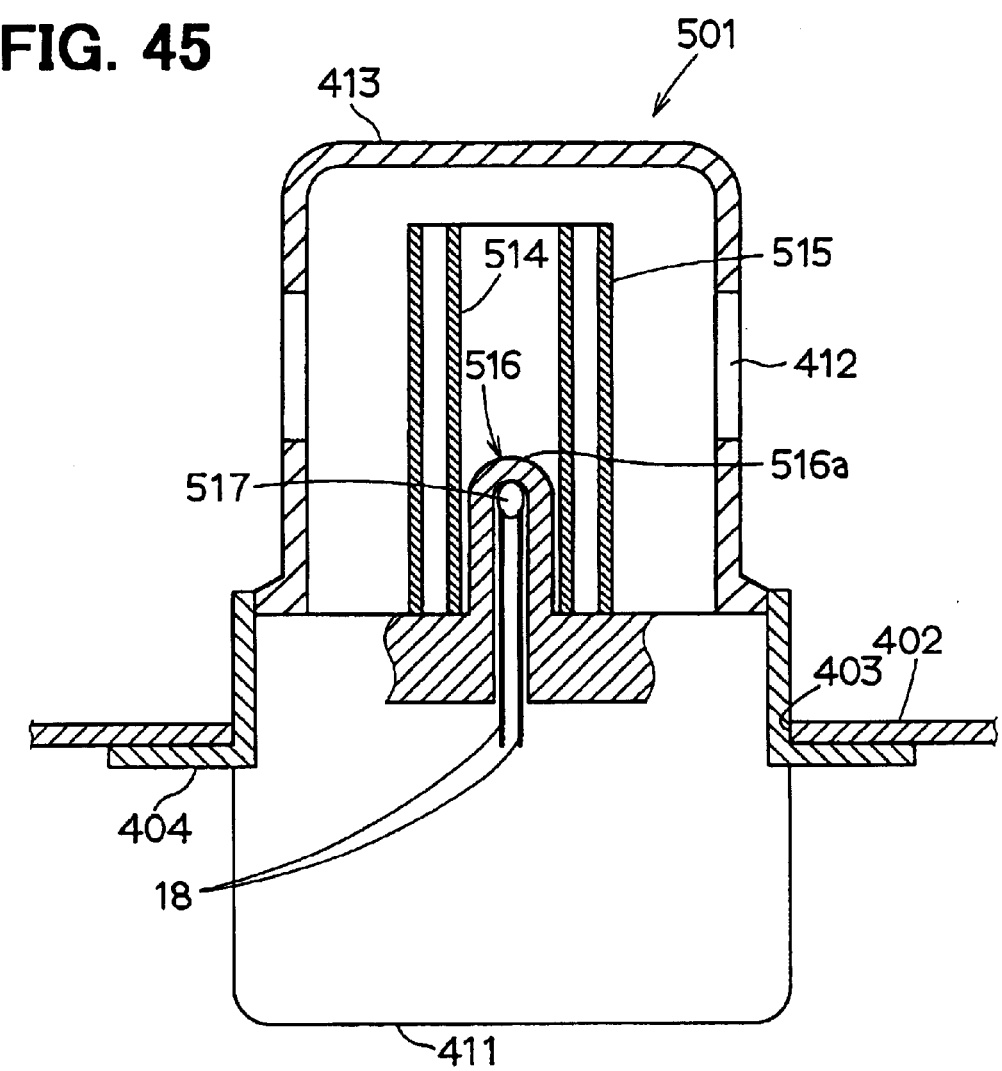
FIG. 45 is a constitutional view of an oil condition sensor according to the nineteenth embodiment of the present invention.

As shown in FIG. 45, an oil condition sensor 501 is mounted in a mounting hole 403 formed in an oil pan 402 by way of a bracket 404.

Figure 46:
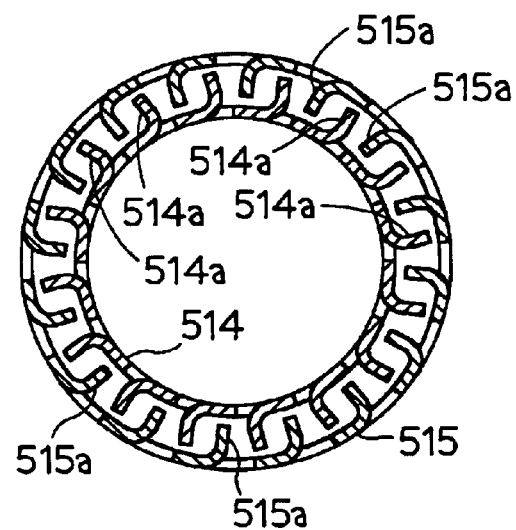
FIG. 46 is a cross-sectional view of a pair of electrodes.

The oil condition sensor 501 includes a housing body portion 411 having the insulating ability and an approximately cylindrical cover body 413 having an oil intake port 412. Further, the oil condition sensor 501 is provided with a pair of electrodes 514 and 515, wherein a pair of electrodes 514 and 515 have respective supporting portions thereof embedded in the inside of the housing body portion 411 and respective supporting portions are electrically connected to terminals by way of wiring. As shown in FIG. 46, a pair of electrodes 514 and 515 are constituted of the inner-lace electrode 514 having a cage shape and the outer-lace electrode 515 also having a cage shape which are arranged concentrically. A plurality of outwardly bent portions 514a of the inner-lace electrode 514 and a plurality of inwardly bent portions 515a of the outer-lace electrode 515 are arranged to face each other in an opposed manner. The inner-lace electrode 514 constitutes a reference electrode formed of a metal electrode made of lead, zinc or the like, for example and the outer-lace electrode 515 constitutes a conductive solid electrode formed of a conductor made of stainless steel having an oxide film, for example. Here, as a reverse case, the inner-lace electrode 514 may constitute a conductive solid electrode and the outer-lace electrode 515 may constitute a reference electrode.

In the inside of the housing body portion 411, a cylindrical housing portion 516 is projected. The cylindrical housing portion 516 is positioned at the inside of the inner-lace electrode 514, and more preferably, along a center axis. An oil temperature sensor 517 is disposed in the inside of a closed distal end portion 516a. The oil temperature sensor 517 is constituted of a thermistor, for example. The wiring 518 of the oil temperature sensor 517 is electrically connected to terminals.

The potential difference corresponding to PH of oil is generated between a pair of electrodes 514 and 515. Further, the oil temperature sensor 517 outputs an electric signal corresponding to the temperature of oil. Here, a pair of electrodes are constituted of the inner-lace electrode 514 and the outer-lace electrode 515 which are arranged concentrically, wherein the oil temperature sensor 517 is positioned in the inside of the inner-lace electrode 514. Accordingly, the temperature of oil in the vicinity of the oil temperature sensor 517 takes a value which extremely approximates the temperature of oil between a pair of electrodes 514 and 515 so that the oil temperature detected by the oil temperature sensor 517 is accurately reflected on the output voltage of the oil condition sensor 501 whereby the proper temperature correction can be performed.

Here, by decreasing the wall thickness of the cylindrical housing portion 516 at least at a portion 516a thereof in the vicinity of the oil temperature sensor 517, the oil temperature can be easily transmitted to the oil temperature sensor 517 so that the detection accuracy of oil temperature can be enhanced.

Figure 47:
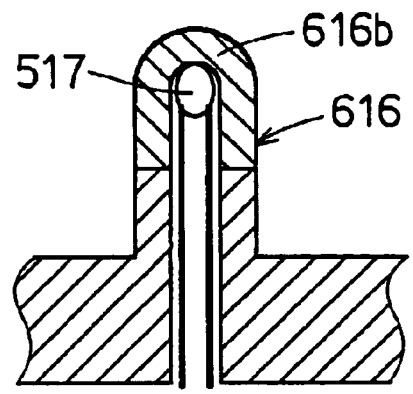
FIG. 47 is a cross-sectional view of an oil condition sensor according to the twentieth embodiment of the present invention.

Further, as shown in FIG. 47, by constituting a portion 616b of a cylindrical housing portion 616 in the vicinity of the oil temperature sensor 517 using a member having favorable thermal conductivity, the detection accuracy of oil temperature can be enhanced in the same manner as the above-mentioned constitution.

Figure 48:
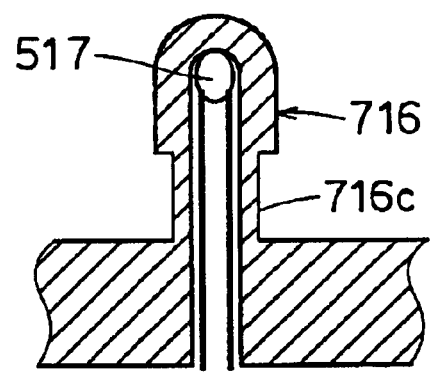
FIG. 48 is a cross-sectional view of an oil condition sensor according to the twenty-first embodiment of the present invention.
Figure 49:
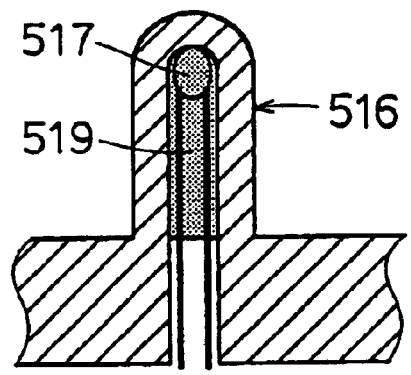
FIG. 49 is a cross-sectional view of an oil condition sensor according to the twenty-second embodiment of the present invention.

Further, as shown in FIG. 48, a cross-sectional area of a supporting portion 716c of a cylindrical housing portion 716 may be set smaller than a cross-sectional area of a distal end side of the cylindrical housing portion 716. Such a constitution can make the conduction of oil temperature to the housing body portion 411 difficult so that the detection accuracy of oil temperature can be enhanced in the same manner. Further, as shown in FIG. 49, a filler 519 may be filled in the inside of the cylindrical housing 516 so as to make the filler 519 cover the oil temperature sensor 517. Compared to a case, in which the oil temperature sensor 517 is covered with an air layer, the conduction of the oil temperature to the oil temperature sensor 517 is facilitated so that the detection accuracy of oil temperature is enhanced and, at the same time, the filler 519 also performs a function of holding the oil temperature sensor 517.

Although the electrodes are formed circular cylindrical shape in the above-described embodiments, the electrodes may be formed in a polygonal shape. Although the electrodes has a plurality of through holes respectively, at least one through hole may improve an introduction of the oil into an oil passage defined between the first and second electrodes.

Although the present invention has been described in connection with the preferred embodiments thereof with reference to the accompanying drawings, it is to be noted that various changes and modifications will be apparent to those skilled in the art. Such changes and modifications are to be understood as being included within the scope of the present invention as defined in the appended claims.

What is claimed is:

1. An oil condition sensor for detecting a condition of oil in response to the potential difference between electrodes, comprising:
   a cylindrical first electrode;
   a cylindrical second electrode which is arranged around an outer periphery of the first electrode substantially coaxially with the first electrode;
   first projections formed by bending respective portions of the cylindrical first electrode to project radially outwardly toward the second electrode side, and thereby defining first communication holes in the cylindrical first electrode; and
   second projections formed by bending respective portions of the cylindrical second electrode to project radially inwardly toward the first electrode side, and thereby defining second communication holes in the cylindrical second electrode,
   wherein the first projections and the second projections are arranged to face each other in an opposed manner as electrodes.

2. The oil condition sensor according to claim 1, wherein the first projections and the second projections are positioned in a circumferentially offset manner.

3. The oil condition sensor according to claim 1, wherein the first projections and the second projections are alternately arranged in the circumferential direction.

4. The oil condition sensor according to claim 1, wherein the first electrode and the second electrode are provided with communication holes which make the inside and the outside of the first electrode and the second electrode communicate with each other.

5. The oil condition sensor according to claim 1, wherein the oil condition sensor further includes a support member formed of an insulation material which supports the first electrode and the second electrode and the first projections and the second projections are disposed away from the support member.

6. An oil condition sensor for detecting a condition of oil in response to the potential difference between electrodes, comprising:
   a cylindrical first electrode;
   a cylindrical second electrode which is arranged around an outer periphery of the first electrode substantially coaxially with the first electrode;
   first projections formed on the first electrode projecting radially outwardly toward the second electrode side;
   second projections formed on the second electrode projecting radially inwardly toward the first electrode side, wherein the first projections and the second projections are arranged to face each other in an opposed manner as electrodes; and
   another pair of electrodes including a first electrode and a second electrode, wherein a plurality of the pairs are coaxially arranged.

7. An oil condition sensor for detecting a condition of oil in response to the potential difference between electrodes, comprising:
   a cylindrical first electrode;
   a cylindrical second electrode which is arranged around an outer periphery of the first electrode substantially coaxially with the first electrode;
   first projections formed on the first electrode projecting radially outwardly toward the second electrode side;
   second projections formed on the second electrode projecting radially inwardly toward the first electrode side, wherein the first projections and the second projections are arranged to face each other in an opposed manner as electrodes; and
   an oil level sensor which detects an oil level is mounted in the inside of the innermost electrode.

8. An oil condition sensor for detecting a condition of oil in response to the potential difference between electrodes, comprising:
   a cylindrical first electrode;
   a cylindrical second electrode which is arranged around an outer periphery of the first electrode substantially coaxially with the first electrode;
   first projections formed on the first electrode projecting radially outwardly toward the second electrode side;
   second projections formed on the second electrode projecting radially inwardly toward the first electrode side, wherein the first projections and the second projections are arranged to face each other in an opposed manner as electrodes; and
   a support member formed of an insulation material which supports the first electrode and the second electrode and the first projections and the second projections are disposed away from the support member, and
   wherein at least one of mounting portions of the first electrode and the second electrode which are mounted on the support member has a portion which is bent to be away from the other mounting portion.

9. An oil condition sensor for detecting a condition of oil in response to the potential difference between electrodes, the oil condition sensor comprising:
   a first electrode;
   a second electrode which generate the potential difference when the first electrode and the second electrode are immersed in oil in the state that the both electrodes face each other in an opposed manner; and a support member which is formed of insulation material and supports the first electrode and the second electrode, wherein at least one of mounting portions of the first electrode and the second electrode which are mounted on the support member has a portion which is bent in a direction away from the other mounting portion.

10. An oil conditions sensor for detecting a condition of oil in response to the potential difference between electrodes, comprising:

a cylindrical first electrode;

a cylindrical second electrode which is arranged around an outer periphery of the first electrode substantially coaxially with the first electrode;

first projections formed on the first electrode projecting radially outwardly toward the second electrode side;

second projections formed on the second electrode projecting radially inwardly toward the first electrode side, wherein the first projections and the second projections are arranged to face each other in an opposed manner as electrodes; and a support member formed of an insulation material which supports the first electrode and the second electrode and the first projections and the second projections are disposed away from the support member, and wherein on a surface of the support member at a side on which both electrodes are mounted, an uneven surface is formed between the first electrode and the second electrode.

11. An oil condition sensor for detecting a condition of oil in response to the potential difference between electrodes, the oil condition sensor comprising:

a first electrode;

a second electrode which generate the potential difference when the first electrode and the second electrode are immersed in oil in the state that the both electrodes face each other in an opposed manner; and a support member which is formed of insulation material and supports the first electrode and the second electrode, wherein on a surface of the support member on which the both electrodes are supported, an uneven surface is formed between the first electrode and the second electrode.

12. An oil condition sensor for detecting a condition of oil in response to the potential difference between electrodes comprising:

a cylindrical first electrode; and a cylindrical second electrode which is arranged around an outer periphery of the first electrode substantially coaxially with the first electrode, wherein portions of a cylindrical surface of the first electrode are bent by an angle of less than 90° toward the second electrode as first fins thus forming communication holes which make the inside and the outside of the cylindrical surface communicate with each other therethrough, portions of a cylindrical surface of the second electrode are bent by an angle of less than 90° toward the first electrode as second fins thus forming communication holes which make the inside and the outside of the cylindrical surface communicate with each other therethrough, and a distance between opposing faces of the fins and a distance between a distal end portion of the each fin and the cylindrical surface of the electrode which faces the fin are set substantially equal.

13. The oil condition sensor according to claim 12, wherein the first fins and the second fins are formed by cutting portions of pre-forms for first and second electrodes and then bending cut portions.

14. The oil condition sensor according to claim 12, wherein a distance between the first electrode and the second electrode is set to not more than 1 mm.

15. The oil condition sensor according to claim 12, further comprising another pair of electrodes including the first electrode and the second electrode, wherein a plurality of the pairs are coaxially arranged.

16. The oil condition sensor according to claim 12, wherein the oil condition sensor further includes a support member which is formed of an insulation material and supports the first electrode and the second electrode thereon, and a contact prevention member which is formed of an insulation material and is disposed at end portions of the first electrode and the second electrode opposite to the support member for preventing the both electrodes from coming into contact with each other.

17. An oil condition sensor for detecting a condition of oil in response to the potential difference between electrodes comprising:

a cylindrical first electrode; and a cylindrical second electrode which is arranged in the outside of the first electrode substantially coaxially with the first electrode, wherein a thickness of a cylindrical wall of the each electrodes is fixed;

cross-sectional shapes of the first electrode and the second electrode on planes which are perpendicular to an axis are similar to each other;

the cylindrical first electrode has first slits that are extended in an axial direction of the cylindrical first electrode; and the cylindrical second electrode has second slits that are extended in an axial direction of the cylindrical second electrode so that the second slits are radially opposed to the first slits.

18. The oil condition sensor according to claim 17, wherein the first electrode and the second electrode are formed of circular cylinders.

19. An oil condition sensor for detecting a condition of oil in response to the potential difference between electrodes comprising:

a cylindrical first electrode;

a cylindrical second electrode which is arranged in the outside of the first electrode substantially coaxially with the first electrode;

first projections formed by bending respective portions of the cylindrical first electrode to project outwardly from the cylinder toward the second electrode, and thereby defining first communication holes in the cylindrical first electrode; and second projections formed by bending respective portions of the cylindrical second electrode to project inwardly from the cylinder toward the first electrode, and thereby defining second communication holes in the cylindrical second electrode, wherein the first projections and the second projections are arranged alternately in the circumferential direction, and a distance which is formed between the one projection out of the first projection and the second projection and the neighboring other projections disposed at both sides of the one projection is set equal to a distance between a distal end of the one projection and a wall surface disposed between the neighboring other projections in the circumferential direction.

20. An oil condition sensor for detecting a condition of oil in response to the potential difference between electrodes comprising:

a cylindrical first electrode;

a cylindrical second electrode which is arranged in the outside of the first electrode substantially coaxially with the first electrode; and a support member which supports the first and second electrodes and is formed of an insulation material, wherein the first and second electrodes include first and second projections which are projected axially from respective one ends of the first and second electrodes, the first and second electrodes are mounted on the support member by connecting the first and second projections to the support member, and the first and second projections are connected to the support member at positions where the first and second projections are offset from each other in the rotational direction with respect to an axis, wherein the oil condition sensor further includes a first wall member which defines a first measurement chamber in which the first and second electrodes are accommodated, and the support member includes a connection surface to which the first and second electrodes are connected, and a hole portion which allows oil to flow along the connection surface is formed in a first wall portion of the first measurement chamber, and wherein the hole portion is formed at a position below the connection surface.

21. An oil condition sensor for detecting a condition of oil in response to the potential difference between electrodes comprising:

a cylindrical first electrode;

a cylindrical second electrode which is arranged in the outside of the first electrode substantially coaxially with the first electrode; and a support member which supports the first and second electrodes and is formed of an insulation material, wherein the first and second electrodes include first and second projections which are projected axially from respective one ends of the first and second electrodes, the first and second electrodes are mounted on the support member by connecting the first and second projections to the support member, and the first and second projections are connected to the support member at positions where the first and second projections are offset from each other in the rotational direction with respect to an axis, wherein the oil condition sensor further includes a first wall member which defines a first measurement chamber in which the first and second electrodes are accommodated, and the support member includes a connection surface to which the first and second electrodes are connected, and a hole portion which allows oil to flow along the connection surface is formed in a first wall portion of the first measurement chamber, and wherein a lower surface among surfaces which define the hole portion is downwardly inclined from the inside to the outside of the first measurement chamber.

22. The oil condition sensor according to claim 21, wherein the inner cylindrical electrode has first projections that are formed by bending corresponding portions of the inner cylindrical electrode so that the first projections of the inner electrode projects radially outwardly toward the second electrode side and thereby form first communication holes in the inner cylindrical electrode, and the outer cylindrical electrode has second projections that are formed by bending corresponding portions of the outer cylindrical electrode so that the second projections of the outer electrode project radially inwardly toward the inner electrode side and thereby form second communication holes in the outer cylindrical electrode.

23. An oil condition sensor comprising:

a cylindrical first electrode;

a cylindrical second electrode which is arranged in the outside of the first electrode substantially coaxially with the first electrode;

a support member which is formed of an insulation material and on which the first and second electrodes are mounted;

an oil level sensor for detecting an oil level which is disposed in the inside of the first electrode;

a first wall portion which defines a first measurement chamber in which the first and second electrodes are arranged, and a first hole portion which introduces oil into the first measurement chamber; and a second wall portion which defines a second measurement chamber in which the oil level sensor is arranged, and a second hole portion which introduces oil into the second measurement chamber from the first measurement chamber, wherein an opening area of the first hole portion is larger than that of the second hole portion.

24. The oil condition sensor according to claim 23, wherein the opening area of the second hole portion is adjusted so that a change speed of an oil level in the inside of the second measurement chamber is lower than a change speed of an oil level in the outside of the second measurement chamber.

25. The oil condition sensor according to claim 23, wherein the oil conditions sensor further includes a temperature sensor which is capable of detecting an oil temperature and the temperature sensor is disposed in the vicinity of the second hole portion in the inside of the second measurement chamber.

26. The oil condition sensor according to claim 25, wherein the oil condition sensor further includes a substrate on which the oil level sensor and the temperature sensor are mounted.

27. An oil condition sensor for detecting a condition of oil in response to the potential difference between electrodes comprising:

a cylindrical first electrode;

a cylindrical second electrode which is arranged in the outside of the first electrode substantially coaxially with the first electrode; and a support member which supports the first and second electrodes and is formed of an insulation material, wherein the first and second electrodes include first and second projections which are projected axially from respective one ends of the first and second electrodes, the first and second electrodes are mounted on the support member by connecting the first and second projections to the support member, and the first and second projections are connected to the support member at positions where the first and second projections are offset from each other in the rotational direction with respect to an axis, wherein the support member includes a body, a columnar body which is projected from the body in a columnar shape to support the oil level sensor, and an annular body which is positioned approximately coaxially with the columnar body and is projected from the body and is formed in an annular shape, the annular body includes at least two opening portions which are arranged to face the columnar body in an opposed manner and have upper open ends, an opening width size L1 of the opening portions is set to L1>L2 with respect to a width size L2 of the columnar body so as to ensure the withdrawing direction of molds which form the columnar body and the annular body, and the body, the columnar body and the annular body are integrally formed.

28. An oil condition sensor comprising:

a pair of inner and outer cylindrical electrodes; and an oil temperature sensor in the inside of the electrodes, wherein the inner and outer cylindrical electrodes have communication holes that are disposed around the oil temperature sensor in a radial direction of the oil temperature sensor.

29. The oil condition sensor according to claim 28, wherein the oil condition sensor further includes a housing which supports a pair of the electrodes and the housing includes a cylindrical portion which is projected along an axis and the oil temperature sensor is disposed in the inside of the cylindrical portion.

30. The oil condition sensor according to claim 29, wherein the cylindrical portion has a thin wall portion at least in the vicinity of the oil temperature sensor.

31. The oil condition sensor according to claim 29, wherein the cylindrical portion has a thin wall portion made of material having a favorable heat conduction at least in the vicinity of the oil temperature sensor.

32. The oil condition sensor according to claim 29, wherein a cross-sectional area of a supporting portion of the cylindrical portion is set smaller than a cross-sectional area of a distal end side of the cylindrical portion.

33. The oil condition sensor according to claim 29, further comprising a filler filled in the inside of the cylindrical portion, the filler covering the oil temperature sensor.

34. An oil condition sensor for detecting a condition of oil in response to the potential difference between electrodes, comprising:

a first electrode made of a metal being formed in a plate shape; and a second electrode made of a different metal that generates potential difference to the first electrode in the oil, the second electrode being formed in a plate shape and being arranged to face the first electrode in parallel with each other, wherein the first and second electrodes define oil passage having a first opening defined between the first and second electrode and a second opening defined by a through hole formed on the first electrode, wherein the first electrode has a fin extended into the oil passage, and the second electrode has a fin extended into the oil passage, the fins being arranged in parallel.

35. An oil condition sensor for detecting a condition of oil in response to the potential difference between electrodes, comprising:

a first electrode made of a metal;

a second electrode made of a different metal that generates potential difference to the first electrode in the oil; and a support member made of resin which supports the first and second electrodes, the support member having a vertical or inclined surface between the first and second electrode.

36. The oil condition sensor according to claim 35, wherein the vertical or inclined surface is provided by an uneven surface formed on the support member.

* * * * *